United States Patent
Levy

(10) Patent No.: US 7,498,309 B2
(45) Date of Patent: Mar. 3, 2009

(54) PHARMACEUTICAL COMPOSITIONS FOR BIOACTIVE PEPTIDE AGENTS

(75) Inventor: Ralph E. Levy, Pleasanton, CA (US)

(73) Assignee: Sangstat Medical Corporation, Cambridge, MA (US)

(*) Notice: Subject to any disclaimer, the term of this patent is extended or adjusted under 35 U.S.C. 154(b) by 257 days.

(21) Appl. No.: 11/000,328

(22) Filed: Nov. 29, 2004

(65) Prior Publication Data

US 2005/0214331 A1 Sep. 29, 2005

Related U.S. Application Data

(60) Provisional application No. 60/525,740, filed on Nov. 29, 2003.

(51) Int. Cl.
*A61K 38/08* (2006.01)
(52) U.S. Cl. .................. 514/15; 424/400; 424/408; 424/455; 424/724; 514/63
(58) Field of Classification Search .............. 514/2, 514/15, 63; 424/400, 408, 455, 724
See application file for complete search history.

(56) References Cited

U.S. PATENT DOCUMENTS

| | | | | |
|---|---|---|---|---|
| 4,287,221 | A | | 9/1981 | Tonedachi et al. |
| 4,643,990 | A | * | 2/1987 | Umehara et al. ............ 514/18 |
| 5,194,376 | A | | 3/1993 | Kang |
| 5,504,068 | A | * | 4/1996 | Komiya et al. ............. 514/11 |
| 5,723,128 | A | * | 3/1998 | Clayberger et al. ...... 424/185.1 |
| 5,733,872 | A | * | 3/1998 | Little ........................ 514/12 |
| 5,753,625 | A | * | 5/1998 | Buelow ...................... 514/13 |
| 5,830,860 | A | * | 11/1998 | Gray et al. .................. 514/12 |
| 5,846,743 | A | * | 12/1998 | Janmey et al. ............... 435/7.8 |
| 5,849,523 | A | | 12/1998 | Afanasiev et al. |
| 5,854,202 | A | * | 12/1998 | Dedhar ...................... 514/2 |
| 6,162,434 | A | | 12/2000 | Buelow |
| 6,190,692 | B1 | * | 2/2001 | Busetti et al. .............. 424/451 |
| 6,214,376 | B1 | | 4/2001 | Gennadios |
| 6,319,518 | B1 | | 11/2001 | Lee et al. |
| 6,475,519 | B1 | * | 11/2002 | Meinzer et al. ............. 424/456 |
| 6,569,463 | B2 | * | 5/2003 | Patel et al. ................ 424/497 |
| 6,613,353 | B1 | * | 9/2003 | Barnwell et al. ........... 424/451 |
| 6,696,545 | B1 | | 2/2004 | Buelow et al. |

FOREIGN PATENT DOCUMENTS

| | | |
|---|---|---|
| WO | WO 94/25068 A1 | 11/1994 |
| WO | WO 95/13288 A1 | 5/1995 |
| WO | WO 95/25504 A1 | 9/1995 |
| WO | 98/00136 * | 1/1998 |
| WO | WO 98/46633 A1 | 10/1998 |
| WO | WO 01/01960 A1 | 1/2001 |
| WO | 03/037379 * | 5/2003 |
| WO | WO 03/061602 A2 | 7/2003 |
| WO | WO 03/061602 A3 | 7/2003 |
| WO | WO 03/072061 A2 | 9/2003 |
| WO | WO 03/072061 A3 | 9/2003 |

OTHER PUBLICATIONS

Walters, P. A. (Proc. Program Int. Symp. Controlled Release Bioact. Mater., 18th (1991), 165-6. Editor(s): Kellaway, Ian W. Publisher: Controlled Release Soc., Deerfield, Ill.).*

Brinkman, B.M., et al., "Engagement of tumor necrosis factor (TNF) receptor 1 leads to ATF-2- and p38 mitogen-activated protein kinase-dependent TNF-α gene expression," *J. Biol. Chem.* 274(43):30882-30886 (Oct. 1999).

Canne, K.E., et al., "Chemical protein synthesis by solid phase ligation of unprotected peptide segments," *J. Am. Chem. Soc.* 121(38):8720-8727 (Sep. 1999).

Cascinu, S., et al., "Management of diarrhea induced by tumors or cancer therapy," *Curr. Opin. Oncol.* 7(4):325-329 (Jul. 1995).

Chapman, S., et al., "Potato virus X as a vector for gene expression in plants," *Plant J.* 2(4):547-557 (Jul. 1992).

Donnelly, M.L., et al., "The cleavage activities of aphthovirus and cardiovirus 2A proteins," *J. Gen. Virol.* 78(Pt 1):13-21 (Jan. 1997).

Donnelly, M.L., et al., "The 'cleavage' activities of foot-and-mouth disease virus 2A site-directed mutants and naturally occurring '2A-like' sequences,"*J. Gen. Virol.* 82(Pt 5):1027-1041 (May 2001).

Farrell, C.L., et al., "Keratinocyte growth factor protects mice from chemotherapy and radiation-induced gastrointestinal injury and mortality," *Cancer Res.* 58(5):933-939 (Mar. 1998).

Greenson, J., et al., "AIDS enteropathy: occult enteric infections and duodenal mucosal alterations in chronic diarrhea," *Ann. Int. Med.* 114(5):366-372 (Mar. 1991).

Kimura, T., et al., "Strategy for the synthesis of large peptides: an application to the total synthesis of human parathyroid hormone [hPTH (1-84)]," *Biopolymers* 20(9):1823-1832 (Sep. 1981).

Kotler, D.P., et al., "Small intestinal injury and parasitic diseases in AIDS," *Ann. Int. Med.* 113(6):444-449 (Sep. 1990).

Muir, T., et al., "Protein synthesis by chemical ligation of unprotected peptides in aqueous solution," *Meth. Enzymol.* 289:266-298 (1997).

Nishiuchi, Y., et al., "Chemical synthesis of the precursor molecule of the Aequorea green fluorescent protein, subsequent folding, and development of fluorescence," *Proc. Natl. Acad. Sci. USA* 95(23):13549-13554 (Nov. 1998).

O'Donnell, M., et al., "Solid-phase synthesis of unnatural amino acids using unactivated alkyl halides," *Tetrahedron Lett.* 38(41):7163-7166 (Oct. 1997).

(Continued)

*Primary Examiner*—David Lukton
(74) *Attorney, Agent, or Firm*—King & Spalding LLP; Todd A. Lorenz

(57) ABSTRACT

Disclosed are pharmaceutical compositions suitable for oral administration of bioactive peptides. Particularly, the pharmaceutical compositions comprise peptides formulated as suspensions stabilized with a dispersing agent. The compositions may be encapsulated in capsules for oral administration. The compositions show improved dissolution characteristics, which are believed to make them suitable for use in the treatment of gastrointestinal disorders.

16 Claims, No Drawings

OTHER PUBLICATIONS

Olson, G., et al., "Concepts and progress in the development of peptide mimetics," *J. Med. Chem.* 36(21):3039-3049 (Oct. 1993).

Precott, S.M., et al., "Cyclooxygenase-2 and carcinogenesis," *Biochim. Biophys. Acta* 1470(2):M69-M78 (Mar. 2000).

Ripka, A., et al., "Peptidomimetic design," *Curr. Opin. Chem. Biol.* 2(4):441-452 (Aug. 1998).

Royo, M., et al., "Solid-phase synthesis of peptides containing α, β-didehydroamino acids," *Eur. J. Org. Chem.* 1:45-48 (Jan. 2001).

Sakakibara, S., "Synthesis of large peptides in solution," *Biopolymers* 37(1):17-28 (1995).

Scott, W., et al., "The solid phase synthesis of α,α-disubstituted unnatural amino acids and peptides (di-UPS)," *Tetrahedron Lett.* 38(21):3695-3698 (May 1997).

Smith, P.D., et al., "Infectious diarrhea in human immunodeficiency virus infection," *Gastroenterol. Clin. North Am.* 17(3):587-598 (Sep. 1988).

Songster, M., et al., "Handles for solid-phase peptide synthesis," *Meth. Enzymol.* 289:129-174 (1997).

Spatola, A., "Peptide Backbone Modifications," in *Chemistry and Biochemistry of Amino Acids Peptides and Proteins*, B. Weinstein (ed.), Marcel Dekker & Co.:New York, NY (1983).

Stewart, J., "Cleavage methods following Boc-based solid-phase peptide synthesis," *Meth. Enzymol.* 289:29-44 (1997).

Suhara, Y., et al., "Peptide-sugar hybrids: Like peptide, like oligosaccharide," *Tetrahedron Lett.* 38(41):7167-7170 (Oct. 1997).

Walker, M., et al., "Protein synthesis by chemical ligation of unprotected peptides in aqueous solution," *Angew. Chem. Int. Ed.* 36(10):1069-1071 (May 1997).

Wipf, P., et al., "Solid-phase synthesis of peptide mimetics with (E)-alkene amide bond replacements derived from alkenylaziridines," *J. Org. Chem.* 62(6):1586-1587 (Mar. 1997).

* cited by examiner

PHARMACEUTICAL COMPOSITIONS FOR BIOACTIVE PEPTIDE AGENTS

1. CROSS REFERENCES TO RELATED APPLICATIONS

This application claims the benefit of U.S. Provisional Patent Application No. 60/525,740, filed Nov. 29, 2003, the entire contents of which is incorporated herein by reference.

2. TECHNICAL FIELD

The present invention relates to a pharmaceutical composition comprising a bioactive peptide suitably formulated for rapid dissolution, and thus particularly suited for oral administration. Described are compositions for treating dysfunctions and diseases of the digestive system, particularly for inflammatory disorders of the gastrointestinal system.

3. BACKGROUND

Solution properties of a peptide are, in part, dependent on the physical and chemical characteristics of each amino acid that make up the peptide and the interaction of each amino acid with other amino acids in the polymer. Amino acids such as leucine, isoleucine, and valine impart hydrophobic character while amino acids such as lysine, histidine, and arginine are hydrophilic. The charge of the peptide, as determined by the acid or base characteristic of the amino acids, will affect solubility properties, depending on the ionization state of the functional group in a particular solvent. Further, hydrogen bonding, ionic, van der Waals, and hydrophobic interactions of the amino acids with the solvent and other amino acids of the polymer impart unique properties to the polymer as a whole.

Many peptides have limited solubility in aqueous solvents owing to the presence of hydrophobic amino acids, and thus may limit the bioactive delivery of such peptides in soluble form. In addition, the presence of hydrophobic domains in a peptide can modify solution behaviour through the hydrophobic effect, where exclusion of water molecules through interaction of hydrophobic domains causes aggregation of the peptide, thereby limiting its solubility and delivery as an active physiological agent. Interactions of excipients with the hydrophobic regions of such peptides can exacerbate the entropy driven aggregation.

The limited solubility of such peptides in aqueous solution and the formation of aggregates from the hydrophobic effect or excipient interactions complicate their delivery as bioactive agents, particularly where rapid dissolution is desirable. Liquid formulations in which the peptides are dissolved or suspended in an aqueous diluent, though available, may suffer from palatability problems due to the unpleasant taste of the peptide. Dilution of the peptide also limits the drug concentrations deliverable by ingestion of peptides dissolved in a liquid. Compressed forms, such as tablets, may provide concentrations sufficient to provide a therapeutic effect but can suffer from slow dissolution properties, particularly by formation of hydration spheres, which can act as barriers for access of solvent molecules to the peptide.

Thus, there is a need in the art for bioactive peptide compositions that overcome the difficulties posed by certain peptide properties, such as insolubility, and have the delivery characteristics to be an effective therapeutic treatment.

4. SUMMARY

The present invention provides for a composition of a bioactive peptide suitably formulated for oral administration and rapid dissolution. Peptides with low solubility in aqueous solutions or peptides that have slow dissolution properties may be delivered using the pharmaceutical compositions herein.

Pharmaceutical compositions of the present invention comprise a bioactive peptide, a suspending agent, and a dispersing agent. The suspending agent is an excipient capable of forming a suspension of the peptide in a suitable medium. Suitable suspending agents in the present compositions include surfactants or polymeric suspending agents. Surfactants may be non-ionic, or ionic such as anionic, cationic, and zwitterionic surfactants.

In the present invention, the pharmaceutical composition comprises a dispersing agent capable of stabilizing the peptide suspensions. Suitable dispersing agent include silicon dioxide, kaolin or bentonite, preferably silicon dioxide in the form of colloidal silicon dioxide.

In the pharmaceutical compositions, the bioactive peptides in the compositions can be any bioactive peptide capable of forming a suspension in the suspending agent. Generally, bioactive peptides will be peptides insoluble or poorly soluble in aqueous solvents, or peptides displaying slow disintegration in an aqueous solvent when presented in a solid or dry form. In the present invention, the pharmaceutical compositions preferably comprise at least one RDP peptide, as disclosed in PCT Publication WO 98/46633; U.S. patent application Ser. No. 08/838,916, filed Apr. 11, 1997; or U.S. Pat. No. 6,696,545.

An exemplary RDP peptide is the RDP58 peptide having the structure:

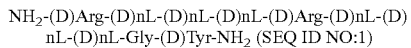
NH$_2$-(D)Arg-(D)nL-(D)nL-(D)nL-(D)Arg-(D)nL-(D)nL-(D)nL-Gly-(D)Tyr-NH$_2$ (SEQ ID NO:1)

where the amidated peptide is in the form of an acetate salt.

The pharmaceutical compositions comprising a peptide, a suspending agent, and a dispersing agent may be compounded in a delivery container, such as a capsule, for oral administration of the peptide.

The pharmaceutical compositions are believed to be particularly useful for treating inflammatory conditions of the gastrointestinal system, particularly intestinal bowel disease, Crohn's disease, or colitis, or inflammatory conditions resulting from cytoablative treatment or HIV infection.

5. DETAILED DESCRIPTION OF PREFERRED EMBODIMENTS

The present invention provides a pharmaceutical composition particularly suited for oral administration of a bioactive peptide. The present invention provides alternative compositions of bioactive peptides in which the compositions display rapid dissolution characteristics, thereby being particularly useful for oral delivery of bioactive peptides having limited solubility in aqueous solvents. The rapid dissolution characteristics are believed to make the compositions particularly suited for treating gastrointestinal disorders.

Attempts to prepare solid compositions of sparingly water-soluble or water-insoluble bioactive peptides as dry blend or dry granulated mixtures with disintegrants, such as starch or cellulose, in compressed tablet compositions have resulted in compositions with slow dissolution times—typically greater than 1 hr—making them less than optimal for delivery to the gastrointestinal system, especially when such peptides are used to treat conditions affecting the upper digestive tract. These slow dissolution times can severely limit the concentration of bioactive peptide for either uptake or therapy. Further, conventional compressed tablet compositions made from wet granulations using disintegrants and surfactant, such as Pluronic F68, a non-ionic surfactant comprised of polyoxyethylene and polyoxypropylene, are found to only marginally improve the dissolution profile.

It is disclosed here that a composition made by suspending the bioactive peptide in a suspending agent facilitates dispersion of the peptide, and provides a pharmaceutical composition with improved dissolution characteristics. The suspension is stabilized by the presence of a dispersing agent, which limits aggregation of the suspensions containing the peptides. By maintaining the bioactive peptides as suspended particles or globules, there is rapid dissolution following administration, thereby providing a composition suitable for administration of a variety of bioactive peptides in oral dosage form.

Exemplary peptides useful in the compositions herein, include, in a preferred embodiment, "RDP peptides" as described in PCT Publication WO 98/46633; U.S. patent application Ser. No. 08/838,916, filed Apr. 11, 1997; or U.S. Pat. No. 6,696,545. These bioactive peptides are believed to be capable of inhibiting the cytotoxic activity of lymphocytic cells, inhibiting the production of inflammatory cytokines and inflammatory responses associated with those cytokines, inhibiting the activity of heme-containing enzymes, and/or delaying the onset of autoimmune disease in a mammal at risk of developing such a disease. These peptides are also believed to have the ability to modulate a variety of biochemical pathways, including p38 MAP kinase, JNK, TRAF, and IRAK mediated signaling, and affect the cellular and physiological processes impacted thereby (see PCT/US2004/015490 and PCT/US2004/015506).

The manifold properties of these bioactive peptides find applications in the treatment of various disorders. In particular, the peptides are believed to be useful for treating inflammatory disorders of the digestive system, particularly intestinal bowel disease, Crohn's disease, and colitis. Other conditions believed to be treatable by the RDP peptides include tissue damage resulting from cytoablative treatments, such as orally administered cytotoxic chemotherapeutic agents used for treating cancers (WO 03/072061). Destruction of the intestinal epithelium by these cytotoxic agents leads to debilitating effects on the affected patient. RDP peptides are also shown to modulate the $CD4^+/CD8^+$ T cell levels in the intestinal mucosal immune system of HIV infected subjects, and believed to be useful in alleviating the wasting and the gastrointestinal inflammation accompanying HIV infection (see PCT/US03/02275).

5.1 Pharmaceutical Compositions

The pharmaceutical compositions of the present invention comprise a bioactive peptide, such as one or more the RDP peptides described below, prepared as a suspension with a suitable suspending agent. The peptide typically has low solubility in the suspending agent and remains as dispersed globules, particles or granules. The compositions further comprise a dispersing agent, which stabilizes and maintains the suspensions by limiting the extent of aggregation or agglomeration of the suspended particles.

Generally, the excipients and peptides form a free flowing suspension that can be compounded into a delivery container, such as a capsule. As used herein, "excipient" refers to a component or an ingredient that is acceptable in the sense of being compatible with other components of the composition and not deleterious to the subject patient or animal to which the composition is to be administered. As used herein "free-flowing suspension" refers to a pourable liquid formulation, such as a liquid suspension.

5.1.1 Suspending Agents and Dispersion Medium

In the present invention, the pharmaceutical compositions comprise at least one suspending agent. Preferably, the suspending agent is an excipient capable of forming a suspension of the bioactive peptide in a defined medium. The term "suspension" as used herein will have the ordinary art recognized meaning and will generally refer to particles or globules dispersed or suspended in free flowing medium, generally a liquid.

The suspending agent may comprise any non-toxic excipient capable of forming a suspension of the bioactive peptides in a dispersion medium. A variety of suspending agents is useful for this purpose. In one aspect, the suspending agent is a surfactant, which may be ionic (e.g., cationic, anionic, zwitterionic) or non-ionic surfactants. Mixtures of surfactants are within the scope of the present invention.

Non-ionic surfactants useful as suspending agents include sorbitan oleate, such as that available under the tradename Arlacel 80; monoolein/propylene glycol, such as that available under the tradename Arlacel 186; $C_8/C_{10}$ fatty acid mono- and diglycerides from coconut oil; citric acid esters of monoglycerides; lactic acid esters of monoglycerides; diacetyl tartaric acid esters of monoglycerides; succinic acid esters of monoglycerides; and sucrose fatty acid esters. Preferred non-ionic surfactants include, but are not limited to, sorbitan oleate, monoolein/propylene glycol, and compatible mixtures thereof.

In another embodiment, the surfactants are trans-esterification products of vegetable oil triglycerides and polyalkylene polyols, as generally described in U.S. Pat. No. 3,288,824. These polyglycolized glycerides include trans-esterification products of various natural (e.g., non-hydrogenated) and/or hydrogenated vegetable oils. Commonly used oils are castor oil, maize oil, apricot kernel oil, almond oil, ground nut oil, olive oil, and palm oil, and mixtures thereof, with polyethylene glycols, in particular polyethylene glycols having an average molecular weight of from about 200 to about 800 daltons. Various forms of trans-esterification product of this defined class are available under the tradename Labrafil. Especially useful as components of the compositions of the invention are oleoyl macrogolglycerides, made by an alcoholysis/tranesterification reaction using apricot kernel oil and PEG 300 (i.e., PEG-6 apricot kernel oil), such as that available under the tradename Labrafil M 1944CS; polyglycolized glycerides made using almond oil and PEG 300 (i.e., PEG-6 almond oil), such as that available under the tradename Labrafil 1966CS; polyglycolized glycerides made using peanut oil and PEG 300 (PEG-6 peanut oil), such as that available under the tradename Labrafil 1969CS; polyglycolized glycerides made using hydrogenated olive oil and PEG 300 (PEG-6 olive oil), such as that available under the tradename Labrafil 1980CS; linoeoyl macroglycerides made by an alcoholysis/transesterification reaction using corn oil and PEG-300 (i.e., PEG-6 corn oil), such as that available under the tradename Labrafil 2125CS; lauryl macroglycerides made by an alcoholysis/esterification reaction using palm kernel oil and PEG 300 (i.e., PEG-6 palm kernel oil), such as that available under the tradename Labrafil M 2130 CS; polyglycolized glycerides made by an alcoholysis/esterification reaction using hydrogenated palm kernel oil and PEG 300 (PEG-8 hydrogenated palm kernel oil), available under the tradename Labrafil M 2130BS; and polyglycolized glycerides made by an alcoholysis/esterification reaction using hydrogenated corn oil and PEG 400 (PEG-8 corn oil), available under the tradename Labrafil WL2609BS. Preferred trans-esterification products include, but are not limited to, PEG-6 apricot kernel oil, PEG-6 almond oil, PEG-6 peanut oil, PEG-6 olive oil, PEG-6 corn oil, PEG-6 palm kernel oil, PEG-8 hydrogenated palm kernel oil, PEG-8 corn oil, and compatible mixtures thereof.

In another embodiment, the surfactant is polyethyloxylated castor oil or derivatives thereof. These compounds are typically mixtures of hydrophobic and hydrophilic components, and generally derived from ethylene glycol reacted with vegetable oils, e.g., polyoxyethylene glycolated natural or hydrogenated castor oils. Preferably, the surfactant is a polyethoxylated hydrogenated castor oil. The surface active substances are available under various tradenames such as Cremophor, Emulphor, Nikkol, and are available having various saponification numbers. These surfactants include, but are not limited to, PEG-35 castor oil (Cremophor EL); PEG-40 hydrogenated castor oil, (Cremophor RH 40); PEG-60 hydrogenated castor oil (Cremophor RH 60); PEG-40 castor oil (Emulphor El-719), PEG-5 hydrogenated castor oil (Nikkol HCO-5), PEG-10 hydrogenated castor oil (Nikkol HCO-10); PEG-20 hydrogenated castor oil (Nikkol HCO-20); PEG-30 hydrogenated castor oil (Nikkol HCO-30); PEG-100 hydrogenated castor oil (Nikkol HCO-100); and PEG 200 castor oil (Eumulgin PRT 200). Preferred polyethoxylated castor oils include, but are not limited to, PEG-35 castor oil, PEG-40 hydrogenated castor oil, PEG-60 hydrogenated castor oil, and compatible mixtures thereof.

Another useful non-ionic surfactant is polyoxyethylene-sorbitan-fatty acid esters (polysorbates), generally produced by co-polymerizing ethylene oxide with fatty acid esters of a sorbitol and its anhydrides of, for example, mono- and trilauryl, palmityl, stearyl and oleyl esters. These are available under the tradename Tween and include, among others, Tween 20, Tween 21, Tween 40, Tween 60, Tween 65, Tween 80, Tween 85, and compatible mixtures thereof.

In a further embodiment, the surfactant may comprise 1,3-polyoxyethylene fatty acid esters, typically produced by reacting fatty acids with ethylene oxide, such as PEG 4-100 monostearates, available under the tradename Myrj and Crodet S; PEG 4-100 monolaurates, available under the tradename Crodet L; PEG 4-100 monooleates, available under the tradename Crodet 0, as well as polyoxyethylene fatty acid esters available under the tradename Cetiol HE. Preferred polyoxyethylene fatty acid esters include, but are not limited to, PEG-8 stearate (Myrj 45), PEG-30 stearate (Myrj 51), PEG-50 stearate (Myrj 53), and compatible mixtures thereof.

Surfactants made of polyoxyethylene-polyoxypropylene co-polymers, also known as poloxamers, are available under the tradenames Pluronic, Emkalyx, and Lutrol. Polymers of this class range from paloxamer 105 to poloxamer 407 and are characterized by the formula $HO(C_2H_4O)_a(C_3H_6O)_b(C_2H_4O)_aH$, where "a" and "b" denote the number of polyoxyethylene and polyoxypropylene units, respectively. These copolymers are available in molecular weights ranging from 1000 to 15000 daltons, and with ethylene oxide/propylene oxide ratios between 0.1 and 0.8 by weight. Specific poloxamers include, among others, poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 238, poloxamer 282, poloxamer 288, poloxamer 331, poloxamer 401, and poloxamer 407. Preferred poloxamers included, but are not limited to, poloxamer 108 (Pluronic F38), poloxamer 188 (Pluronic F68), poloxamer 217 (Pluronic F77), poloxamer 238 (Pluronic F88), poloxamer 288 (Pluronic F98), poloxamer 407 (Pluronic F127), and compatible mixtures thereof.

Another type of surfactant useful in the compositions is propylene glycol fatty acid esters such as, among others, propylene glycol monocaprylate, propylene glycol dicaprylate, propylene glycol dicaprate, propylene glycol dicaprylate dicaprate, propylene glycol dilaurate, propylene glycol hydroxystearate, propylene glycol isostearate, propylene glycol laurate, propylene glycol ricinoleate, propylene glycol stearate, propylene glycol dioctanoate, and propylene glycol ricinoleate. Various propylene glycol fatty acid esters are available under the tradename Miglyol. Preferred propylene glycol fatty acid esters include, but are not limited to, C8/C10 triglyceride (Miglyol 132) and propylene glycol dicaprylate dicaprate (Miglyol 840), and compatible mixtures thereof.

Other lipohilic surfactants include include mono-, di- and mono/di-glycerides, examples of which include, among others, monopalmitolein, monoelaidin, monocaproin, monocaprylin, monolaurin, glyceryl monomyristate, glycerol monooleate/linoleate, glycerol monolinoleate, glycerol monostearate, glyceryl mono- and dioleate, and especially esterification products of caprylic or capric acid with glycerol. Products of caprylic or capric acid are caprylic/capric acid mono- and di-glycerides, including but not limited to, glyceryl laurate, glyceryl citrate/lactate/oleate/linoleate, glyceryl caprylate, glyceryl caprylate/caprate, caprylic acid mono- and diglycerides, caprylic/capric glycerides, such as those available under the tradename Imwitor. An exemplary surfactant of this type is Imwitor 742, which is the esterification product of a mixture of caprylic acid and capric acid with glycerol. Preferred mono-, di- and mono/di-glycerides include, but are limited to, glyceryl laurate, glyceryl citrate/lactate/oleate/linoleate, glyceryl caprylate, glyceryl caprylate/caprate, caprylic acid mono- and diglycerides, caprylic/capric glycerides, and compatible mixtures thereof.

Polyglycerol esters of fatty acids are also suitable surfactants for the present invention. Among the polyglyceryl fatty acid esters, preferred hydrophobic surfactants include polyglyceryl oleate (Plurol Oleique), polyglyceryl-2 dioleate (Nikkol DGDO), and polyglyceryl-10 trioleate. Preferred surfactants include polyglyceryl-10 laurate (Nikkol Decaglyn 1-L), polyglyceryl-10 oleate (Nikkol Decaglyn 1-O), polyglyceryl-10 mono, dioleate (Caprol.RTM. PEG 860), and compatible mixtures thereof.

Surfactants made of monoglycerides, for example, glycerol monooleate, glycerol monopalmitate and glycerol monostearate, are available under the tradenames Myvatex, Myvaplex and Myverol, and acetylated forms (e.g., mono- and di-acetylated monoglycerides) available under the trade name Myvacet.

In a further embodiment, the surfactant may be sorbitan fatty acid esters, for example such as those available under the tradename Span (Atlas/ICI). Sorbitan fatty acid esters include, among others, sorbitan monolaurate (Span-20), sorbitan monopalmitate (Span-40), sorbitan monooleate (Span-80), sorbitan monostearate (Span-60), sorbitan trioleate (Span-85), sorbitan sesquioleate (Arlacel), sorbitan tristearate (Span-65), sorbitan monoisostearate (Crill 6), and sorbitan sesquistearate (Nikkol SS-15). Preferred sorbitan fatty acid esters include, but are not limited to, sorbitan monolaurate. sorbitan monopalmitate, sorbitan monooleate, sorbitan monostearate, sorbitan trioleate, and sorbitan tristearate.

Surfactants with sterol groups or its derivatives include cholesterol and corresponding derivatives, in particular phytosterols, for example sitosterol, campesterol or stigmasterol, and ethylene oxide adducts thereof. Ethylene oxide adducts of sterols include, but are not limited to, PEG-24 cholesteryl ether (Solulan C-24), PEG-30 cholestanol (phytosterol GENEROL series), PEG-25 phytosterol (Nikkol BPSH-25), PEG-5 soyasterol (Nikkol BPS-5), PEG-10 soyasterol (Nikkol BPS-10), PEG-20 soyasterol (Nikkol BPS-20), and PEG-30 soyasterol (Nikkol BPS-30). Preferred sterol based surfactants include, but are not limited to, stigmasterol and PEG-30 cholestanol.

The surfactants may also be ionic surfactants, which include anionic, cationic, and zwitterionic surfactants. Typical anionic surfactants useful in the compositions include fatty acids salts and bile salts. Exemplary ionic surfactants include, but are not limited to, sodium oleate, sodium lauryl sulfate, sodium lauryl sarcosinate, sodium cholate, and sodium taurocholate. Other types of ionic surfactants include phospholipids, phosphtidylcholine, phosphatidic acid, lecithin and its various derivatives, alginate salts; alkyl benzene sulfone, acyl taurates, hexadecyl triammonium bromide, cetyl trimethyl ammonium bromide, trialkylglycine, and alkyl benzyldimethylammonium salts.

In another aspect, the suspending agent is a hydrophilic polymer, particularly polyethylene oxide polymers (e.g., polyethylene glycol). As used herein, polyethylene oxide polymers of PEG refers to a polymer having the general formula $H(OCH_2CH_2)_nOH$. Generally, each PEG is designated by the average number of "n" units or its average molecular weight in daltons. Various molecular weights of polyethylene glycol polymers are known in the art, including, PEG 200 (n=4), PEG 300 (n=6), PEG 400 (n=8), PEG 600 (n=12), PEG 900, PEG 1000 (n=20), PEG 1450 (n=32), PEG 3350 (n=75), PEG 4500 (n=100), and PEG 8000 (n=150). Preferably, the polyethylene glycol polymers are polymers PEG 200 to PEG 600, which have a range of molecular weights of from about 190 to about 630 daltons. Preferred polyethylene glycol include, but are not limited to, PEG 200, PEG 300, PEG 400, and PEG 600.

It is to be understood that choosing a suitable suspending agent is well within the ordinary skill of those in the art. Factors to be considered include the physical properties (e.g., hydrophobicity, hydrophilicity, etc.), the solubility, and stability of the bioactive peptide in the suspending agent.

The suspensions may be made in a medium suitable for forming suspensions using the suspending agents described herein. An optional dispersion medium is an aqueous solution, such as sterile non-pyrogenic water, saline, or an aqueous solution containing a suitable buffering agent. Other optional mediums for use in the process, such as solutions of lower alkyl alcohols, may be used depending on the nature of the suspending agent chosen. Lower alkyl alcohols include, by way of example and not limitation, methanol, ethanol or propanol, or mixtures thereof.

5.1.2 Dispersing Agent

In the present invention, the pharmaceutical compositions further comprise a dispersant or a dispersing agent. As used herein, a dispersant or dispersing agent is an agent capable of stabilizing the suspension and limiting aggregation of the suspended particulates. Suitable dispersing agents are non-toxic pharmaceutically acceptable dispersing agents and include but are not limited to thickening agents.

In the present invention, exemplary dispersing agents include, by way of example and not limitation, silicon dioxides, and derivatives of silicon dioxides, such as alkylated silica gels and colloidal silicon dioxide, such as those available under the trade name Aerosil (e.g., Aerosil 130, 200, 300, 380, O, OX50, TT600, MOX 80, MOX 170, LK 84 and methylated Aerosil R 972) or CAB-O-SIL®. Preferred dispersing agents include, but are not limited to, silicon dioxides and derivatives of silicone dioxides and compatible mixtures thereof, more preferably colloidal silicon dioxide.

In another aspect, the dispersing agents may be bentonite, a hydrated aluminum silicate found in certain types of clay and which is in the form of colloidal particles of about 50-150 microns and numerous particles of about 1-2 microns. A similar dispersing agent is kaolin, another type of aluminum silicate, also found in certain naturally occurring clays. Other dispersing agents may include hectorite, magnesium aluminium silicate, magnesium oxide. Preferred dispersing agents include but are not limited to bentonite, kaolin, magnesium aluminium silicate, magnesium oxide, and compatible mixtures thereof.

In another aspect, the dispersing agents are thickening agents. Suitable thickening agents include but are not limited to dextrin, alginates, propylene glycol alginate, and zinc stearate. Also finding use as thickening agents are water-soluble celluloses and cellulose derivatives including, among others, alkyl celluloses, such as methyl-, ethyl-, and propyl-celluloses; hydroxyalkyl-celluloses, such as hydroxypropyl celluloses and hydroxypropylalkylcelluloses; acylated celluloses, such as cellulose acetates, cellulose acetatephthallates, cellulose-acetate succinates and hydroxypropylmethyl-cellulose phthalates; and salts thereof, such as sodium carboxymethyl celluloses. Useful celluloses are available under the tradenames Klucel and Methocel. Preferred thickening agents include but are not limited to alginates, hydroxypropyl celluloses, hydroxypropylmethylcellulose phthalates, sodium carboxymethyl celluloses, and compatible mixtures thereof.

Other dispersing agents suitable for use in the pharmaceutical formulations will be known to those of ordinary skill in the art, and are to be included within the scope of the compositions described herein (see, e.g., *Handbook of Pharmaceutical Excipients*, $4^{th}$ Ed, (Kibbe, A. H. ed.) Washington D.C., American Pharmaceutical Association (2003)).

5.1.3 Bioactive Peptides

The pharmaceutical compositions disclosed herein will generally comprise at least one bioactive peptide. As used herein, "peptide" refers to at least two covalently attached amino acids, which includes polypeptides, and oligopeptides. The peptide may be made up of naturally occurring amino acids and peptide bonds, or synthetic peptidomimetic structures. Thus, "amino acid" or "peptide residue" as used herein means both naturally occurring and synthetic amino acids. For example, homo-phenylalanine, citrulline, and norleucine are considered amino acids for the purposes of the invention. "Amino acids" also includes imino residues such as proline and hydroxyproline. The side chains may be either the D- or L-configuration, or combinations thereof. Thus, the peptides may have one or more D-isomer amino acids, up to all of the amino acids of the peptide being the D-isomer. Although the bond between each amino acid is typically an amide or peptide bond, it is to be understood that peptide also includes analogs of peptides in which one or more peptide linkages are replaced with other than an amide or peptide linkage, such as a substituted amide linkage, an isostere of an amide linkage, or a peptide or amide mimetic linkage (see, e.g., Spatola, "Peptide Backbone Modifications," in *Chemistry and Biochemistry of Amino Acids Peptides and Proteins*, Weinstein, ed., Marcel Dekker, New York (1983); Olson, G. L. et al, *J. Med. Chem.* 36:3039-3049 (1993); and Ripka and Rich, *Curr. Opin. Chem. Biol.* 2:441-452 (1998)). Bioactive peptide refers to a peptide displaying a physiological, pharmacological or prophylactic effect on a cell or subject, and thus will encompass therapeutic peptides.

Various bioactive peptides may be formulated in the manner described herein. Typically, the bioactive peptides useful in the compositions will generally be less than about 100 amino acids, less that about 50 amino acids, or less than about 20 amino acids in length. However, it is to be understood that the pharmaceutical compositions may be applied to peptides greater than 100 amino acids where delivery of such peptides are desired and where the pharmacological activity of the peptide is substantially preserved in the compositions.

In one aspect, bioactive peptides may be peptides that have low solubility or are insoluble in an aqueous solution, typically water. In one embodiment, the peptide is sparingly water-soluble or substantially water-insoluble, which refers to a solubility requiring at least about 30 parts solvent to dissolve 1 part solute at ambient temperature. In another embodiment, the peptide is practically water-insoluble or water-insoluble, which refers to a solubility requiring at least about 10,000 parts solvent per 1 part solute at ambient temperature (see, e.g., *Remington: the Science and Practice of Pharmacy*, Vol 1, pg 194-195 (Gennaro, ed.) (1995)). Thus, for the present purposes, a peptide is sparingly water soluble or substantially water insoluble if the solubility is less than about 33 mg/ml at ambient temperature and water insoluble or practically insoluble if the solubility is less than about 0.1 mg/ml at ambient temperature. The sparingly soluble or water insoluble peptides form suspended particulates in presence of the suspending agent, thereby allowing rapid dissolution of the peptide in solution.

The bioactive peptide is typically an isolated or purified peptide. As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The phrase "substantially free of chemical precursors or other chemicals" includes preparations of the peptide in which it is separated from chemical precursors or other chemicals that are involved in its synthesis. Preparations of a peptide are substantially free of precursors in preparation having less than about 30% (by dry weight) chemical precursors or other chemicals, less than about 20% chemical precursors or other chemicals, less than about 10% chemical precursors or other chemicals, or less than about 5% chemical precursors or other chemicals.

Exemplary bioactive peptides for use in the compositions herein are referred to as "RDP peptides" as disclosed in PCT Publication WO 98/46633 or U.S. Pat. No. 6,696,545. The core sequence of the RDP peptides includes two basic amino acids separated by from three to four hydrophobic amino acids, particularly three hydrophobic amino acids, and particularly where the N-terminus is a basic amino acid. Preferably, the C-terminal amino acid is an aromatic amino acid, particularly tyrosine. Of particular interest is where at least one of the peptide core terminal amino acids is a peptide terminal amino acid, which may be in the monomeric or oligomeric form of the compound.

Preferred RDP peptides for use in the pharmaceutical compositions and methods of the present invention may comprise peptides having the sequence B-X-X-X-B-X-X-X-J-Tyr (SEQ ID NO:2), where B is a basic amino acid, preferably Lys or Arg, particularly Arg on at least one position, preferably at both positions; J is Gly, B or an aliphatic hydrophobic amino acid of from 5 to 6 carbon atoms, particularly Gly or B; and X is an aliphatic or aromatic amino acid. In one embodiment, at least three X amino acid residues are the same non-polar aliphatic amino acid, preferably at least four are the same non-polar aliphatic amino acid, more preferably at least five are the same non-polar aliphatic amino acid, and more preferably, all are the same non-polar aliphatic amino acid. In a preferred embodiment, the non-polar aliphatic amino acids are of from 5 to 6 carbon atoms, particularly 6 carbon atoms, particularly the non-polar aliphatic amino acids Val, Ile, Leu, and nL. Thus, in some embodiments, X is any amino acid other than a charged aliphatic amino acid, and preferably any amino acid other than a polar aliphatic amino acid.

Of the six amino acids indicated by X in the B-X-X-X-B-X-X-X-J-Tyr (SEQ ID NO:2) peptide sequence, preferably at least 3 are aliphatic amino acids of from 5 to 6 carbon atoms, more preferably at least 4 are aliphatic amino acids of from 5 to 6 carbon atoms, most preferably at least 5 are aliphatic amino acids of 5-6 carbon atoms, more particularly 6 carbon atoms. In a preferred embodiment, the aliphatic amino acids are non-polar aliphatic amino acids of from 5 to 6 carbon atoms, particularly Val, Ile, Leu, and nL. The other amino acids may be other uncharged aliphatic amino acids, particularly non-polar aliphatic amino acids or aromatic amino acids.

Compositions of particular interest will include an RDP peptide having the sequence Arg-U-X-X-Arg-X-X-X-J-Tyr (SEQ ID NO:3) wherein all of the symbols have been defined previously except U, which comprises an uncharged aliphatic amino acid or aromatic amino acid, particularly a non-polar aliphatic amino acid or aromatic amino acid.

The amino acids may be the L-amino acids or D- isomers thereof. Consequently, the peptides may have one or more D-stereoisomer amino acids, up to all of the amino acids, except when the amino acid is Gly, which does not occur as the L- or D-isomer.

For the purposes of this invention, the amino acids are defined in the following categories:

```
1. Aliphatic
    (a) non-polar aliphatic:
        Gly, Ala, Val, nL, Ile, Leu
    (b) polar aliphatic:
        (1) uncharged:
            Cys, Met, Ser, Thr, Asn, Gln
        (2) charged:
            Asp, Glu, Lys, Arg 2. Aromatic
        Phe, His, Trp, Tyr
``` wherein Pro may be included in the non-polar aliphatic amino acids, but will normally not be included. "nL" represents norleucine, where the non-polar aliphatic amino acids may be substituted with other isomers.

Exemplary RDP peptides include the following:

| 1 | Arg-Leu-Leu-Leu-Arg-Leu-Leu-Leu-Gly-Tyr | SEQ ID NO:4 |
|---|---|---|
| 2 | Arg-Val-Leu-Leu-Arg-Leu-Leu-Leu-Gly-Tyr | SEQ ID NO:5 |
| 3 | Arg-Ile-Leu-Leu-Arg-Leu-Leu-Leu-Gly-Tyr | SEQ ID NO:6 |
| 4 | Arg-Leu-Val-Leu-Arg-Leu-Leu-Leu-Gly-Tyr | SEQ ID NO:7 |
| 5 | Arg-Leu-Tle-Leu-Arg-Leu-Leu-Leu-Gly-Tyr | SEQ ID NO:8 |
| 6 | Arg-Leu-Leu-Val-Arg-Leu-Leu-Leu-Gly-Tyr | SEQ ID NO:9 |

-continued

| 7 | Arg-Leu-Leu-Ile-Arg-Leu-Leu-Leu-Gly-Tyr | SEQ ID NO:10 |
| 8 | Arg-Leu-Leu-Leu-Arg-Val-Leu-Leu-Gly-Tyr | SEQ ID NO:11 |
| 9 | Arg-Leu-Leu-Leu-Arg-Ile-Leu-Leu-Gly-Tyr | SEQ ID NO:12 |
| 10 | Arg-Leu-Leu-Leu-Arg-Leu-Val-Leu-Gly-Tyr | SEQ ID NO:13 |
| 11 | Arg-Leu-Leu-Leu-Arg-Leu-Ile-Leu-Gly-Tyr | SEQ ID NO:14 |
| 12 | Arg-Leu-Leu-Leu-Arg-Leu-Leu-Val-Gly-Tyr | SEQ ID NO:15 |
| 13 | Arg-Leu-Leu-Leu-Arg-Leu-Leu-Ile-Gly-Tyr | SEQ ID NO:16 |
| 14 | Arg-Trp-Leu-Leu-Arg-Leu-Leu-Leu-Gly-Tyr | SEQ ID NO:17 |
| 15 | Arg-Leu-Trp-Leu-Arg-Leu-Leu-Leu-Gly-Tyr | SEQ ID NO:18 |
| 16 | Arg-Leu-Leu-Trp-Arg-Leu-Leu-Leu-Gly-Tyr | SEQ ID NO:19 |
| 17 | Arg-Leu-Leu-Leu-Arg-Trp-Leu-Leu-Gly-Tyr | SEQ ID NO:20 |
| 18 | Arg-Leu-Leu-Leu-Arg-Leu-Trp-Leu-Gly-Tyr | SEQ ID NO:21 |
| 19 | Arg-Leu-Leu-Leu-Arg-Leu-Leu-Trp-Gly-Tyr | SEQ ID NO:22 |
| 20 | Arg-Tyr-Leu-Leu-Arg-Leu-Leu-Leu-Gly-Tyr | SEQ ID NO:23 |
| 21 | Arg-Leu-Tyr-Leu-Arg-Leu-Leu-Leu-Gly-Tyr | SEQ ID NO:24 |
| 22 | Arg-Leu-Leu-Tyr-Arg-Leu-Leu-Leu-Gly-Tyr | SEQ ID NO:25 |
| 23 | Arg-Leu-Leu-Leu-Arg-Tyr-Leu-Leu-Gly-Tyr | SEQ ID NO:26 |
| 24 | Arg-Leu-Leu-Leu-Arg-Leu-Tyr-Leu-Gly-Tyr | SEQ ID NO:27 |
| 25 | Arg-Leu-Leu-Leu-Arg-Leu-Leu-Tyr-Gly-Tyr | SEQ ID NO:28 |
| 1nL | Arg-nL-nL-nL-Arg-nL-nL-nL-Gly-Tyr | SEQ ID NO:1 | nL = norleucine

Preferred in the pharmaceutical compositions are the RDP peptides having the amino acid sequence B-nL-nL-nL-B-nL-nL-nL-J-Tyr (SEQ ID NO:31), where, as above, B is a basic amino acid, preferably Arg or Lys, more preferably Arg; J is Arg, Lys or Gly, preferably Gly; and nL is norleucine. An exemplary RDP peptide comprises the RDP58 peptide having the sequence Arg-nL-nL-nL-Arg-nL-nL-nL-Gly-Tyr (SEQ ID NO:1). The amino acids of the peptide may be the L or D isomer. Thus, one or more of the amino acids, up to all of the amino acids of the peptide, may be the D isomer.

The terminal amino group or carboxyl group may be modified by alkylation, amidation, or acylation to provide esters, amides or substituted amino groups, where the alkyl or acyl group may be of from about 1 to 30, usually 1 to 24, preferably either 1 to 3 or 8 to 24, particularly 12 to 18 carbon atoms. The peptide or derivatives thereof may also be modified by acetylation or methylation to alter the chemical properties, for example lipophilicity. Methods for acylating, and specifically for acetylating the free amino group at the N-terminus are known in the art. Accordingly, for the C-terminus, the carboxyl group may be modified by esterification with alcohols or amidated to form —$CONH_2$, CONHR, or CONR, wherein each R is a hybroxycarbyl (1-6 carbons) (see T. E. Creighton, *Proteins: Structure and Molecular Properties*, W. H. Freeman & Co. San Francisco, Calif., (1983)).

The peptide may be present in the form of a salt, generally in a salt form which is pharmaceutically acceptable. These include, by way of example and not limitation, inorganic salts of sodium, potassium, lithium, ammonium, calcium, magnesium, iron, zinc, copper, and manganese. Various organic salts of the peptide may also be made with, including, but not limited to, acetic acid, propionic acid, pyruvic acid, maleic acid, succinic acid, tartaric acid, citric acid, benozic acid, cinnamic acid, and salicylic acid.

A particularly preferred embodiment of an RDP peptide, RDP58, has the following structure:

$NH_2$-(D)Arg-(D)nL-(D)nL-(D)nL-(D)Arg-(D)nL-(D)nL-(D)nL-Gly-(D)Tyr-$NH_2$
(SEQ ID NO:1)

where (D) refers to the D-isomer, and where the amidated peptide is in the form of an acetate salt.

It is to be understood that although the inventive compositions are suitable for formulating RDP peptides, the pharmaceutical compositions may be used for other peptides having "structurally similar characteristics". By "structurally similar" is meant a peptide, oligopeptide, or polypeptide with an amino acid sequence, although not identical to those described above, is sufficiently similar in structure to display one or more therapeutic effects of the RDP peptides.

Structurally similar peptides include the known peptides from the HLA-B $\alpha_1$-domain, particularly the amino acids from 75 to 84 and variations of this sequence where not more than 2 amino acids are replaced (see, e.g., WO 95/13288 and U.S. Pat. No. 6,162,434). Also included are sequences based on the human TCR-$\alpha$ transmembrane region consisting of that sequence and sequences having not more than 2 mutations from that sequence (see Australian Application Nos. PN 0589 and PN 0590, filed Jan. 16, 1995). These sequences include 2 basic amino acids, where the 2 basic amino acids are separated by 4 aliphatic hydrophobic amino acids, although the application indicates that from 3 to 5 hydrophobic amino acids may be present. By mutation is intended each substitution of one amino acid for another or an insertion or deletion, each being counted as one mutation.

As will be appreciated by those skilled in the art, other bioactive peptides that are capable of forming suspension in the suspending agents may be used in the formulations described herein.

5.1.4 Additives

In the present invention, various additives may be added to the pharmaceutical compositions. These include, but are not limited to, anti-oxidants, stabilizing agents, flavoring agents, sweeteners, preservatives, anti-microbial agents, and coloring agents.

Antioxidants protect peptides containing methionine, cysteine, histidine, tryptophane and tyrosine from oxidation or photooxidation. Exemplary antioxidants that may be useful in the compositions include, but are not limited to, ascorbic acid, ascorbyl palmitate, tocopherols, butyl hydroxy anisole, butyl hydroxyl toluene, and chelating agents (e.g., EDTA). When present, these may be in an amount of about 0.1 to about 5% and preferably about 0.5 to about 1% of the total weight of the composition.

Sweetening or flavoring agents, when present, may be in an amount of from 0.5 to 20% by weight based on the total weight of the composition. Exemplary sweetening agents include, but are not limited to, dextrose, mannitol, saccharin, sorbitol, sucrose, aspartame, or xylitol. Others will be known to the skilled artisan.

The pharmaceutical compositions optionally contain coloring agents, water-soluble dyes or pigments, and opacifiers. Typical coloring agents include, among others, synthetic iron oxides, e.g., Sicopharm Yellow 10, Sicopharm Brown 70, FD&C Red, and FD&C Blue, while titanium dioxide serves as an exemplary opacifying agent.

It is to be understood that the choice of the additives will be compatible with the suspensions and will limit any undesirable effects on the pharmaceutical compositions. Determining the compatibility of other excipients and additives is within the skill of those in the art.

5.2 Dosage Forms and Capsules

For the compositions provided herein, the amount of bioactive peptide in the compositions is a therapeutically or pharmaceutically effective amount.

The pharmaceutical compositions can be provided in various forms, such as in the form of a solution, in single unit dosage form, and multiunit dosage form. The suspension may be provided in packets, ampules, bottles, and other types of containers, and where appropriate, accompanied by a device, such as a gradated cup, pipette, or syringe for providing a measured liquid dose. The liquid forms may be for oral administration, although other methods of administration, such as topical, vaginal, or rectal are contemplated where appropriate.

In a further aspect, the compositions are provided as a semi-solid dispersion or a liquid suspension, compounded in orally administrable hard or soft capsules, or other encapsulated dosage forms known in the art. Capsules may be made from various materials, including, by way of example and not limitation, gelatin, polysaccharide (e.g., starch, agar, pectin, hydroxypropyl methylcellulose, hydroxyethycellulose, etc.), or mixtures thereof (see, e.g., U.S. Pat. No. 6,319,518). The capsule compositions may also include a plasticizer, such as glycerin, triacetin, sorbitol, polyethylene glycol, propylene glycol, citrate, and phthalate, to impart form and flexibility where desired. Capsules from non-gelatin substitute, carrageen, are described in U.S. Pat. No. 6,214,376. Capsule materials are chosen to be compatible with the fill material (e.g., peptide suspension). Exemplary encapsulates are based on gelatin, which is typically derived from animal skin by hydrolysis with an acid (type A gelatin) or derived from bones and animal skin by hydrolysis with an alkaline solution (type B gelatin). An exemplary gelatin capsule composition is described in the Examples.

An enteric coating may be present on the final encapsulate to limit rapid dispersion within the stomach, which may be useful when targeting the bioactive peptide to the small intestine or colon. The enteric coating remains intact in the stomach but dissolves in the intestine, where the pH is higher than the gastric environment. Various enteric coatings are known in the art, a number of which are commercially available. Coatings include, by way of example and not limitation, those based on methacrylic acid-methacrylic acid ester copolymers, polymer cellulose ether, cellulose acetate phthalate, polyvinyl acetate phthalate, and hydroxypropyl methyl cellulose phthalate. The enteric coating is applied using a variety of methods known in the art, such as spraying or layering (see, e.g., U.S. Pat. No. 4,287,221). The thickness of the enteric coating is designed based on the nature of the coating material and the desired lag time or delay in release of the pharmaceutical composition.

In a further aspect, a lubricant or release agent may be used to facilitate processing of the encapsulate and improve capsule handling characteristics. Suitable lubricants include, among others, magnesium stearate, hydrogenated vegetable oil, sodium stearyl fumarate, glyceryl palmitostearate, calcium stearate, medium chain triglyceride (e.g., Miglyol 812), and phosphoglycerides (e.g., lecithin). Mixtures of lubricants may be used, such as a mixture of medium chain triglyceride and phosphoglyceride. In addition, coloring agents, such as those described above, may be used for the capsule component of the pharmaceutical compositions.

5.3 Preparation of the Compositions

The pharmaceutical compositions described herein can be made by means conventional in the art, including, mixing, dissolving, granulating, densifying, levigating, emulsifying, suspending, dispersing, encapsulating, entrapping and/or lyophilizing processes. Guidance and general methods are described in *Remington's Pharmaceutical Sciences,* 17th Ed., Mack Publishing Co., Philadelphia, Pa., (1985) and Handbook of Pharmaceutical Excipients, supra.

The present invention further provides methods of preparing the pharmaceutical compositions of a bioactive peptide. A suitable method comprises admixing the bioactive peptide and a suspending agent to form a liquid suspension of the peptide. The dispersing agent may be added during or following formation of the suspension, preferably following formation of the suspension.

Synthesis of bioactive peptides may use any chemical synthetic techniques known in the art for the preparation of the peptides and peptide analogs. In one aspect, the compositions may be prepared using conventional solution or solid phase peptide synthesis and standard chemistries. Use of amino acid analogues derivatized for use in standard synthesis chemistries, including D-isomer amino acids, or modifications following peptide synthesis may be used to generate peptide analogues. General synthetic methods are described in "Solid Phase Peptide Synthesis" in *Methods in Enzymology* (Fields, G. B. Ed.) Academic Press, San Diego (1997) and Lloyd-Williams, P. et al., *Chemical Approaches to the Synthesis of Peptides and Proteins*, CRC Press, Boca Raton. (1997). Other references describing synthesis of peptides and peptide analogues include, among others, Wipf, P. and Henninger, T. C., *J. Org. Chem.* 62:1586-1587 (1997); Wellings, D. A. and Atherton, E., "Standard Fmoc protocols," in *Methods Enzymol.* 289, 44-67 (1997); Walker, M. A., *Angew. Chem. Int. Ed.* 36, 1069-1071 (1997); Suhara, Y. et al., *Tetrahedron Lett.* 38:7167-7170 (1997); Songster, M. F. and Barany, G., "Handles for solid-phase peptide synthesis," in *Methods Enzymol.* 289, 126-174 (1997); Scott, W. L. et al., *Tetrahedron Lett.* 38, 3695-3698 (1997); O'Donnell, M. J. et al., *Tetrahedron Lett.* 38:7163-7166 (1997); Muir, T. W. et al., "Protein synthesis by chemical ligation of unprotected peptides in aqueous solution," in *Methods Enzymol.* 289:266-298 (1997); Royo, M. et al., *Eur. J. Org. Chem.* 45-48 (2001)); and Stewart, J. M., "Cleavage methods following Boc-based solid-phase peptide synthesis," *Methods Enzymol.* 289:29-44 (1997)).

In another embodiment, the bioactive peptides may be prepared by way of segment condensation (Kimura, T. et al., *Biopolymers* 20:1823-1832 (1981); Sakakibara, S., *Biopolymers* 37:17-28 (1995); and Canne, L. E. et al., *J. Am. Chem. Soc.* 121:8720-8727 (1999)). In segment condensation, peptide segments of the final peptide product are synthesized separately and then assembled to form the full length peptide product (see, e.g., Nishuchi, Y. et al., *Proc. Natl. Acad. Sci. USA* 95:13549-13554 (1998)). Depending on the synthetic strategy, solution or solid phase based ligation of the peptide segments may be used.

As noted above, the terminal amino group or carboxyl group of the peptide may be modified by alkylation, amidation, or acylation to provide esters, amides or substituted amino groups, where the alkyl or acyl group may be of from about 1 to 30, usually 1 to 24, preferably either 1 to 3 or 8 to 24, particularly 12 to 18, carbon atoms. The peptide or derivatives thereof may also be modified by acetylation or methylation to alter the chemical properties, for example lipophilicity. Other modifications include deamination of glutamyl and asparaginyl residues to the corresponding glutamyl and aspartyl residues, respectively; hydroxylation of proline and lysine; phosphorylation of hydroxyl groups of serine or threonine; and methylation of amino groups of lysine, arginine, and histidine side chains (see, e.g., Creighton, T. E., *Proteins: Structure and Molecular Properties*, W. H. Freeman & Co. San Francisco, Calif. (1983)).

Where appropriate, the peptides may also be synthesized using recombinant DNA methods. For recombinant production, a polynucleotide sequence encoding the peptide is inserted into an appropriate expression vehicle, i.e., a vector that contains the necessary elements for the transcription and translation of the inserted coding sequence, or in the case of an RNA viral vector, the necessary elements for replication and translation. The expression vehicle is then introduced into a suitable target cell which will express the peptide. Depending on the expression system used, the expressed peptide is then isolated by procedures well-established in the art. Methods for recombinant protein and peptide production are known in the art (see, e.g., Sambrook et al., *Molecular Cloning A Laboratory Manual*, 3$^{rd}$ Ed., Cold Spring Harbor Laboratory, N.Y. (2001); and Ausubel et al., *Current Protocols in Molecular Biology*, Greene Publishing Associates and Wiley Interscience, N.Y. (1989), updates to 2004).

To increase efficiency of production, the polynucleotide can be designed to encode multiple units of the peptide separated by enzymatic or chemical cleavage sites. Either homopolymers (i.e., repeating peptide units) or heteropolymers (i.e., different peptides strung together) can be engineered in this way. The resulting polypeptide can be cleaved (e.g., by treatment with the appropriate enzyme or chemical cleavage reagent) in order to recover the peptide units. This can increase the yield of peptides driven by a single promoter. For example, where methionine or tryptophane is absent, an intervening methionine or tryptophane may be incorporated, which allows for single amino acid cleavage using CNBr or BNPS-Skatole (2-(2-nitrophenylsulfenyl)-3-methyl-3-bromoindolenine), respectively. Alternatively, cleavage is accomplished by use of sequences that are recognized by particular proteases for enzymatic cleavage or sequences that act as self-cleaving sites (e.g., 2A sequences of apthoviruses and cardioviruses) (see, e.g., Donnelly, M. L., *J. Gen. Virol.* 78: 13-21 (1997) and Donnelly, M. L., *J. Gen. Virol.* 82: 1027-41 (2001)). In another embodiment, a polycistronic polynucleotide can be designed so that a single mRNA is transcribed which encodes multiple peptides (i.e., homopolymers or heteropolymers) each coding region operatively linked to a cap-independent translation control sequence; e.g., an internal ribosome entry site (IRES). When used in appropriate viral expression systems, the translation of each peptide encoded by the mRNA is directed internally in the transcript; e.g., by the IRES. Thus, the polycistronic construct directs the transcription of a single, large polycistronic mRNA which, in turn, directs the translation of multiple, individual peptides. This approach eliminates the production and enzymatic processing of polyproteins and may significantly increase yield of peptide driven by a single promoter.

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems infected with recombinant virus expression vectors (e.g., retrovirus, adenovirus, adeno-associated virus, lentivirus, etc.) or transformed with recombinant plasmid expression vectors.

The vector elements in the expression systems may vary in their strength, degree of specificity, and the type of organism. Depending on the host/vector system, any number of appropriate transcription and translation regulatory elements comprise the expression vector, including inducible and non-inducible promoters, enhancer or transcriptional activator sequences, ribosomal binding sites, CAP sequences, transcriptional start and stop sequences, translational start and stop sequences, selectable markers, secretory sequences, and the like. For cloning and expression in bacterial systems, inducible promoters include bacteriophage $\lambda$ $P_L$ promoter, plac, ptrp, ptac and the like may be used.

In another embodiment, the expression vectors are used to express the proteins in yeast cells. Yeast expression systems are known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL promoters (e.g., GAL 1, GAL 4, GAL 10. etc.), the promoters from alcohol dehydrogenase (ADH or ADC1), enolase, glucokinase, glucose-6-phosphate isomerase, glyceraldehyde-3-phosphate-dehydrogenase, hexokinase, phosphofructokinase, 3-phosphoglycerate mutase, pyruvate kinase, fructose bisphosphate, acid phosphatase gene, tryptophase synthase (TRP5) and copper inducible CUP1 promoter. Any plasmid containing a yeast compatible promoter, an origin of replication, and termination sequences is suitable.

In another embodiment, the expression vectors are used for expression in plants. Plant expression vectors are known in the art. Vectors are known for expressing genes in *Arabidopsis thaliana*, tobacco, carrot, and maize and rice cells. Suitable promoters for use in plants include those of plant or viral origin, including, but not limited to, CaMV 35S promoter (active in both monocots and dicots; Chapman, S. et al., *Plant J*. 2, 549-557 (1992)) nopoline promoter, mannopine synthase promoter, soybean or *Arabidopsis thaliana* heat shock promoters, tobacco mosaic virus promoter (Takmatsu, et al., *EMBO J*. 6: 307 (1987)), and AT2S promoters of *Arabidopsis thaliana* (e.g., PAT2S1, PATS2, PATS3 etc.).

In a further embodiment, the expression vectors are used to express the proteins in insect cells. Expression vectors for the transformation of insect cells, and in particular, baculovirus vectors used to create recombinant baculoviruses for expressing foreign genes, are known in the art (see, e.g., O'Reilly, D. R. et al., *Baculovirus Expression Vectors: A Laboratory Manual*, W.H. Freeman & Co, New York, (1992)). By "baculovirus" or "nuclear polyhedrosis viruses" as used herein is meant expression systems using viruses classified under the family of baculoviridae, preferably subgroup A. These include expression systems specific for *Bombix, Autographica*, and *Spodoptera* (see, e.g., U.S. Pat. No. 5,194,376). Other expression systems include *Amsacta moorei* entomopoxvirus (AmEPV), *Aedes aegypti* desonucleosis (*Aedes* DNV, U.S. Pat. No. 5,849,523), and *Galleria mellonella* densovirus (Tal, et al., *Arch. Insect Biochem. Physiol.* 22: 345-356 (1993)).

It is to be understood that other expression systems for producing bioactive peptides by recombinant methods will be apparent to those skilled in the art.

The bioactive peptides can be purified by various art-known techniques. Standard purification methods include electrophoretic, immunological, and chromatographic techniques, including ion exchange, hydrophobic, affinity, size exclusion, reverse phase HPLC, and chromatofocusing. The proteins may also be purified by selective solubility, for instance in the presence of salts or organic solvents. The degree of purification necessary will vary depending on the intended use of the bioactive peptides. Thus, in some instances no purification will not be necessary.

For the pharmaceutical compositions, peptides are prepared as dispersible powders or granules suitable for forming the suspension. Granules or particles may be formed by a wet or dry granulation process, layering techniques or other suitable manufacturing methods. This may include precipitating or lyophilizing the peptide and milling to generate the powder or granule. As further described in detail herein, an exemplary method uses densified peptide, which is made by mixing the peptide with alcohol, drying the mixture, and then passing it through a screen or a series of screens to form granules.

The relative proportions of the ingredients in the pharmaceutical composition will vary depending on the particular type of composition made. Determining the proportions of the components is within the capability of the skilled artisan. Generally, the bioactive peptide will be present in an amount of from about 5% to about 70%, preferably from about 10% to about 70%, and more preferably about 15% to about 60% by weight based on the total weight of the composition, which is the weight of the pharmaceutical composition excluding the weight of the capsule.

The suspending agent, such as Labrafil M 1944, will generally be present in an amount from about 25% to about 95%, preferably from about 50% to about 90%, and more preferably about 60% to about 85% by weight based on the total weight of the composition. The percentages of the peptide and suspending agent are proportioned to generate a liquid, free flowing suspension.

The amount of dispersing agent will vary depending on the amount required to stabilize the suspension, the consistency required, for example flowability for filling into a capsule or other suitable container, and the nature of the dispersing agent chosen. As a general guide, a dispersing agent, such as colloidal silicon dioxide, is present up to about 20%, preferably from about 0.5% to about 10%, more preferably from about 0.5% to about 5% by weight of the total weight of the composition. An exemplary dispersing agent, silicon dioxide product Aerocil 300, may typically be present from about 0.5% to about 2.0% % by weight of the total weight of the composition.

The foregoing proportions of the compositions are understood as being preferred and not limiting the compositions of the present invention. A person skilled in the art can use different proportions and achieve compositions of bioactive peptides with similar dissolutions characteristics as described herein. Additives, e.g., preservatives, flavoring agents, antimicrobial agents, and/or coloring agents, may be added to the suspension to the desired levels.

Once a suspension is formed, it may be packaged into containers, such as bottles, ampules, in single unit or multi-unit dosages. For oral administration, the peptide suspensions may be placed into capsules, as described above, preferably soft gelatin capsules. A release agent and/or lubricant is added to the capsule to enhance dissolution of the capsule and to optimize storage and its handling characteristics. Capsules may be packaged into bottles or blisters packs.

5.4 Kits

The present invention also provide for kits comprising the pharmaceutical compositions of bioactive peptides. The kits include the suspensions of the bioactive peptide in packaged forms, as described above, and for liquid formulations, a device for measuring the dosage. As noted above, the device may include, among others, a gradated cup, pipette, or syringe. The kit may have additional components, including instructions for administration and information on drug effects. Instructions and information may be in any medium, including, but not limited to, print, tape, computer disc, and/or optical disc.

5.5 Uses of the Pharmaceutical Compositions

The pharmaceutical compositions of the present invention are used to deliver a therapeutically effective amount of any bioactive peptide that can be prepared as a suspension. By "pharmacologically effective amount" or "pharmacologically effective dose" or "therapeutic dose" is an amount sufficient to produce the desired physiological effect or amount capable of achieving the desired result, particularly for treating the disorder or disease condition, including reducing or eliminating one or more symptoms or manifestations of the disorder or disease.

By "treatment" herein is meant therapeutic or prophylactic treatment, or a suppressive measure for the disease, disorder or undesirable condition. Treatment encompasses administration of the subject peptides in an appropriate form prior to the onset of disease symptoms and/or after clinical manifestations, or other known disease manifestations, of the condition to reduce disease severity, halt disease progression, or eliminate the disease. Prevention of the disease includes prolonging or delaying the onset of symptoms of the disorder or disease, preferably in a subject with increased susceptibility to the disease.

The amount administered to the host will vary depending the form of the pharmaceutical composition (e.g., capsule or liquid suspension), the purpose of the administration, such as prophylaxis or therapy, the state of the host, the manner of administration, the number of administrations, interval between administrations, and the like. These can be determined empirically by those skilled in the art and may be adjusted for the extent of the therapeutic response. Factors to consider in determining an appropriate dose include, but are not limited to, size and weight of the subject, the age and sex of the subject, the severity of the symptom, the stage of the disease, method of delivery of the agent, half-life of the peptide agents, and efficacy of the bioactive peptides. Stage of the disease to consider includes whether the disease is acute or chronic, relapsing or remitting phase, and the progressiveness of the disease. Another factor to consider is the likelihood of undue adverse side effects, e.g., toxicity, irritation, or allergic response, commensurate with a reasonable benefit/risk ratio for the subject being administered to. Determining the dosages and times of administration for a therapeutically effective amount are within the ambit of a person having ordinary skill in the art.

Although the pharmaceutical compositions herein are suited for oral delivery, either in the form of a liquid suspension or capsule, it is to be understood that the compositions may be administered by other modes as long as the desired therapeutic effect is achieved. Thus, the liquid forms may be administered rectally or vaginally for conditions involving the corresponding organs. In another aspect, the suspensions may also be applied topically to the skin for treating inflammatory conditions, such as psoriasis. Other applications will be apparent to the skilled artisan.

A preferred class of the bioactive peptide are the RDP peptides described herein. This class of bioactive peptides are believed to affect production of various cytokines, particularly TNF-α, IFN-γ, IL-2 and IL-12. Cytokine TNF-α is a key mediator of acute and chronic inflammatory response, acting in the response by recruiting and activating macrophages, affecting migration of leukocytes, causing induction of nitrous oxide (NO) production and vasodilation, and inducing cellular apoptosis. Although produced mainly by mononuclear phagocytes, TNF is also produced by other cells types, such as $Th_1$ helper cells, B cells, natural killer cells, mast cells, neutrophils, astrocytes, and glial cells. IFN-γ is another cytokine mediating a variety of physiological responses, including the inflammatory response. IFN-γ is involved in stimulating development of CD4+ cells into $Th_1$ helper cells, which play a role in cell mediated immunity and delayed type hypersensitivity reactions. The IFN-γ released by $Th_1$ cells also regulates the $Th_2$ response. IFN-γ also recruits leukocytes to a site of infection and activates the phagocytic activity of macrophages.

The cytokines IL-2 and IL-12 function in conjunction with other cytokines in modulating the immune response. IL-2, also known as T-cell growth factor (TGF), is secreted by stimulated CD4+ T helper cells, cytotoxic CD8+ T-cells, and granular lymphocytes. It promotes proliferation and differentiation of additional CD4+ cells and B-cells, and is also known to activate macrophages and oligodendrocytes. IL-2 is also an inducer of pro-inflammatory cytokines such as IL-1, TNF-α, and IFN-γ. IL-12 is produced mainly by macrophages and B-cells and promotes synthesis of IFN-γ and proliferation of natural killer, $Th_1$ and cytotoxic CD8+ T-cells. Thus, the dysregulation of IL-2 and IL-12 cytokines is associated with a variety of inflammatory disorders.

Because of the intimate connection between TNF-α, IFN-γ, IL-2 and IL-12 in promoting development of cell mediated immunity and delay hypersensitivity, perturbations in the production of these cytokines is correlated with dysregulation of the immune response and its attendant consequences, such as inflammatory diseases and autoimmune reactions. The believed ability of the RDP peptides in modulating the production of these cytokines may make the compositions of the present disclosure particularly applicable for treating such conditions.

Another property of the RDP peptides, which appears independent of the cytokine modulating effect, is its believed ability to inhibit heme-oxygenase activity. Heme oxygenase is an initial and rate-limiting enzyme involved in the degradation of heme into carbon monoxide (CO), iron, and biliverdin. The biliverdin is subsequently converted to bilirubin by biliverdin reductase. Of the known forms of heme-oxygenase (e.g., HO-1, HO-2, and HO-3), the HO-1 isoform is ubiquitously distributed in mammalian tissues and is strongly and rapidly induced by a variety of stimuli and agents that cause oxidative stress and pathological conditions. HO-1 induction is important in the response of tissues to oxidative stress and inflammation and promotes protection against free radical-mediated injury and modulation of pro- and anti-inflammatory cytokines. Inhibitors of heme-oxgenase activity, including the RDP peptides, are known to induce HO-1, thereby being useful as therapeutic agents for protecting against oxidative cell injury and amelioration of the damaging effects of inflammatory response.

In addition to the cytokine and heme enzyme modulating activities, the multifaceted RDP peptides are also believed to display activity against various signal transduction pathways, including signaling mediated by JNK and p38 MAPK, and the corresponding activity of NF-κB, as further described below. Since the biological activity of the cytokine TNF-α appears to depend on JNK and p38 MAPK activation, inhibiting the signaling mediated via these pathways is another mechanism by which the RDP peptides are useful in modulating the inflammatory response (see, e.g., Brinkman, B. M. et al., *J. Biol. Chem.* 274:30882 (1999)).

Thus, the pharmaceutical compositions herein are believed to be applicable to the treatment of a variety of conditions characterized by acute or chronic inflammation, autoimmune reactions, and/or oxidative injury. As the compositions are particularly suited for oral administration, the compositions find use in treating injury and inflammation of the digestive system, particularly the gastrointestinal system, which includes oral cavity, larynx, esophagus, stomach, small intestine, and large intestine. Conditions treatable with the compositions include, by way of example and not limitation, inflammatory bowel disease, Crohn's disease, and colitis (e.g., ulcerative colitis) (see U.S. Pat. No. 6,696,545; WO 98/46633; PCT/US2004/015506). Other types of inflammatory conditions of the digestive system include oral submucous fibrosis, gastroesophageal reflux disease (GERD), Barret's disease, gastritis, proctitis, and the like.

In a further embodiment, the pharmaceutical compositions are administered to subject undergoing cytotoxic chemotherapeutic treatment or exposure to ionizing radiation. Gastrointestinal tissue injury and inflammation resulting from cytoablative treatments, such as oral administration of chemotherapeutic agents or radiation therapy used for treating cancers can lead to debilitating effects on the affected patient. Gastrointestinal toxicity characterized by severe mucositis and diarrhea often limits both the dose and duration of cytoablative therapy. Cytoablative doses of chemotherapy or radiotherapy compromise the absorptive and barrier action of the mucosa by killing the crypt stem cells, thereby impairing normal regeneration (Farrell, C. L. et al., *Cancer Res.* 58:933-39 (1998)). As the damaged cells slough, the mucosa becomes thin and denuded, accompanied by delayed cellular renewal, mucosal atrophy, inflammation and often ulceration. Hence patients undergoing cytoablative therapies frequently develop enteric mucositis and diarrhea, which can be debilitating and lethal (Cascinu, S., *Curr. Opin. Oncol.* 7:325-29 (1995)). Moreover, the gastrointestinal effects of these cytoablative therapies can be aggravated and prolonged by the lack of enteral intake that frequently occurs. Anorexia, mucositis, abdominal cramps, diarrhea with food intake and the reliance on intravenous therapy (which suppresses appetite) all compromise the exposure of the gut to enteral nutrients, thus limiting the body's ability to stimulate normal intestinal epithelial proliferation. The tissue-protective and anti-inflammatory properties of the RDP peptides are believed to be useful in ameliorating these deleterious effects arising from the cytoablative treatments (see WO 03/061602).

In another embodiment, the pharmaceutical compositions are used to treat subjects infected with HIV, particularly as an adjunct to treatment with anti-retroviral compounds. There appears to be two effects of the RDP peptides in ameliorating the effects of HIV viral infection. First, the peptide appears to modulate the CD4+/CD8+ T cell levels in the mucosal immune system of HIV infected subjects when administered adjunctively with an HIV antiviral compound. The ratio of CD4+/CD8+ T cells in the gut-associated lymphoid tissue of HIV infected subjects typically tend towards a low ratio because of the depletion of CD4+ cells. However, it is believed that in subjects treated with a combination of RDP peptides and antiviral compound, the T cell ratio rebounds towards more normal levels, thereby leading to a more balanced T cell population and restoration of the immune system in the gut. Second, the RDP peptides may alleviate the wasting and the gastrointestinal inflammation associated with HIV infection. With the onset of immunodeficiency, opportunistic enteric pathogens may contribute to the severity of intestinal disease in infected individuals (Smith, P. D. et al., *Gastroenterol Clin. North Am.* 17(3):587-598 (1988); Kotler, D. P. et al., *Ann. Intern. Med.* 113(6):444-449 (1990); Greenson et al., *Ann. Intern. Med.* 114(5):366-72 (1991)). However, in many instances, intestinal abnormalities are often occur prior to advanced stages of immunodeficiency and in the absence of detectable enteric pathogens Given that the onset of the intestinal mucosal immune system dysregulation may occur early in infection and contribute to debilitating effects of HIV infections, the pharmaceutical compositions are believed to be suitable for use in treatment for the wasting encountered by many HIV patients.

Other applications of the pharmaceutical compositions herein are indicated by the believed ability of the RDP peptides to modulate various signal transduction mediated by integrins and the TNF family receptors (see PCT/US2004/015506 and PCT/US2004/015490), particularly through activities of MyD88, IRAK, TRAF, MEK, MEKK, Ras, Rac, CDC42, Rho, c-src, Akt, JNK, ERK, PI3K, p38MAPK, NF-κB, AP-1, paxillin, FAK, Fyn, Pyk2, PLCγ, and p53, in mammalian cells. The integrin signaling affected by the RDP peptides is preferably the signal transduction leading to the activation of the transcription factors AP1 and NF-κB. Preferably, the integrin signaling is βIII integrin signaling. Disease conditions related to the activity of any of these signal transduction pathways may be treated by the pharmaceutical compositions.

In another aspect, the pharmaceutical compositions may be useful for treating periodontitis, which occurs when inflammation or infection of the gums (gingivitis) spreads to the ligaments and bone that support the teeth, thereby resulting in destruction of teeth. It is believed that the RDP peptides, through their effects on signaling via RANK (a member of the TNF receptor superfamily) and intermediary signaling complex MyD88/IRAK/TRAF, are believed to increase the activity of osteoblasts while decreasing the activity of osteoclasts. RDP peptides are also believed to be able to decrease osteoclast differentiation and bone resorption, thereby providing a mechanism for ameliorating the effects of periodontitis.

In another aspect, the compositions herein may be used in methods for decreasing vascularization of a cell population in vivo, and particularly for decreasing angiogenesis related to tumor formation and maintenance. Angiogenesis includes both sprouting and non-sprouting angiogenesis. In a further embodiment, the compositions may be suitable in reducing the metastatic and invasive potential of a tumor, particularly metastatic tumor, which includes tumors that have metastasised or tumors that have not yet metastasized but have been determined to have metastatic potential. Particular types of tumors that may be treated by the compositions may be any cancer of the digestive system. These include, among others, tumors of the oral cavity (lips, gums, tongue, palate, etc.), oropharynxlarynx, esophagus, stomach, small intestine, and large intestine (i.e., colorectal). Types of cancers include, adenocarcinoma, squamous cell carcinoma, sarcoma, cylindroma, and lymphoma.

In addition to its believed use in treatments for diagnosed cases of cancer, in yet a further embodiment, the pharmaceutical compositions may be used prophylactically to reduce the occurrence of tumors or delay tumor progression. It is known that there is an intimate association of chronic inflammation and oxidative tissue injury to tumorigenesis. Activation of neutrophils, eosinophils, and macrophages result in generation of reactive oxygen species (e.g., superoxide, hydrogen peroxide, and hydroxyl radical) and nitrogen intermediates (e.g., peroxynitrite, peroxynitrous acid, etc.). Although these reactive compounds serve a protective function by killing bacteria and parasites, they also cause tissue damage (e.g., lipid peroxidation) and DNA modification, which can lead to genetic mutations. Chronic inflammation leads to increased production of reactive oxygen and nitrogen species, and thus enhanced rates of DNA modifications in the affected tissues. Another contributing factor to tumor formation by the inflammatory response is the activity of lipid mediators, particularly prostaglandins. Production of these mediators not only leads to spiralling activation of the inflammatory response, thereby facilitating the cell damaging effects, but also promotion of angiogenesis. It is believed that inhibition of the rate limiting enzyme in prostaglandin synthesis, COX-2, which is overexpressed in adenocarcinomas of the colon, may prevent or decrease the incidence of tumor progression (see, e.g., Prescott, S. M. et al., *Biochim. Biophys. Acta* 1470:M69-M78 (2000)). Finally, the cytokines produced during chronic inflammation may further contribute to tumor formation by generating cytokines that promote cell division and proliferation, stimulate of immune cells to generate reactive oxygen and nitrogen species, and promotion of angiogenesis, such as by inducing synthesis matrix metalloproteases. The prophylactic uses for delaying or preventing tumor formation arises from the property of the RDP peptides in protecting against oxidative cell injury via induction of HO-1 activity, inhibition of pro-inflammatory cytokine, modulation of signalling pathways associated with activation of the inflammatory response, and inhibition of biochemical pathways associated with angiogenesis. In particular, the oral compositions may be administered to affect tumors formation and progression in the organs of the digestive system, such a esophageal cancer, which in one aspect is associated with inflammatory conditions induced by gastroesophageal reflux disease, and colorectal cancer, which in one aspect is associated with Crohn's disease and ulcertative colitis. Other parts of the digestive system may be prophylactically treated similarly to delay tumor formation or progression.

6. EXAMPLE

6.1 Example 1

Peptide Synthesis

Peptide synthesis. Peptides were synthesized by synthesizing intermediary peptides and assembling the shorter peptides to generate the full-length peptide. Synthesis used standard tBoc chemistry and Boc protected amino acids.

Intermediate peptide Boc-(D)Arg-(D)nL-(D)nL-(D)nL-OH (SEQ ID NO:29) was synthesized using HCL-(D)nL-OMe and sequential addition of Boc-(D)nL-OH, Boc-(D)nL-OH, and Boc-(D)Arg-OH. The intermediary peptide Gly (D)Tyr-NH$_2$ was synthesized by coupling Boc-Gly-OH to HCl-(D) Tyr-NH$_2$. Peptide Boc-(D)Arg-(D)nL-(D)nL-(D)nL-OH (SEQ ID NO:29) is then coupled to Gly (D)Tyr-NH$_2$ to form Boc-(D)Arg-(D)nL-(D)nL-(D)nL-Gly (D)Tyr-NH$_2$ (SEQ ID NO:1). The product is then coupled to Boc-(D)Arg-(D)nL-(D)nL-(D)nL-OH (SEQ ID NO:29) to generate a crude preparation of the full length peptide NH$_2$-(D)Arg-(D)nL-(D)nL-(D)nL-(D)Arg-(D)nL-(D)nL-(D)nL-Gly-(D)Tyr-NH$_2$ (SEQ ID NO:1).

Synthesis of peptide SF1257-02 (Boc-(D)nL-(D)nL-OMe): A solution of HCl.(D)Nle-OMe (1.02 eq) in a mixture of DMF and ethyl acetate is neutralized with TEA (1.02 eq) at −5±2° C. HOBt (1 eq). A solution of Boc-(D)Nle-OH (1 eq) and EDAC (1.1 eq) are then added to the mixture at −5±2° C. The pH is maintained at 6-6.5 with TEA. After about 1 h, the reaction mixture is allowed to warm up to reach room temperature. The reaction completion is monitored by TLC. The reaction mixture is diluted with ethyl acetate and washed with a 10% KHSO$_4$ solution, a 5% NaHCO$_3$ solution, and brine. The organic phase is evaporated in vacuo and the oily residue dried by azeotropic distillations with toluene. The final oil is dissolved in toluene. Removal of the Boc protecting group is done by adding TFA (A×3.2 L) at temperature below 15° C. to a solution of the Boc-(D)Nle-(D)Nle-OMe (A kg) in toluene, and the reaction mixture is allowed to warm up to room temperature. The cleavage completion is monitored by TLC. The reaction mixture is evaporated in vacuo and residual TFA is removed by azeotropic distillations with toluene. The deprotected peptide product (SF1257-03) is precipitated in diisopropyl ether, filtered, washed with diisopropyl ether and dried in vacuo.

Synthesis of SF1257-04 (Boc-(D)nL-(D)nL-(D)nL-OMe): A solution of TFA.(D)Nle-(D)Nle-OMe (1 eq) in DMF is neutralized with TEA at −5±2° C. HOBt (1 eq), Boc-(D)Nle-OH (1 eq) in DMF, and then EDAC (1.2 eq) is added to the mixture at −5±2° C. After about 30 minutes, the pH is adjusted to 6.5-7 with TEA. After allowing the mixture to react for about 30 min, the mixture is allowed to warm up to reach room temperature. Reaction completion is monitored by TLC. The product is precipitated in processed water, filtered, and washed with processed water. The solid is dried in vacuo. Protecting group is removed by slowly adding a solution of TFA (A×3.2 L) at below 15° C. to a solution of Boc-(D)Nle-(D)Nle-(D)Nle-OMe (A kg) in toluene below 15° C. The reaction mixture is allowed to warm up to room temperature. After completion of cleavage (as monitored by TLC and HPLC), the reaction mixture is evaporated in vacuo and residual TFA is removed by azeotropic distillations with toluene. The deprotected peptide (SF1257-05) is precipitated in diisopropyl ether, filtered, washed with diisopropyl ether, and dried in vacuo.

Synthesis of SF1257-06 (Boc-(D)Arg-(D)nL-(D)nL-(D)nL-OMe) (SEQ ID NO:29): A solution of TFA.(D)Nle-(D)Nle-(D)Nle-OMe (1 eq) in DMF is adjusted to pH 8.5 with TEA(1 eq) at −5±2° C. HOBt (0.88 eq), Boc-(D)Arg-OH.HCl.H$_2$O (1 eq) and then EDAC (1.26 eq) are added to the mixture at −5±2° C. After about 30 minutes, the pH is adjusted to 6.5-7 with TEA and the temperature is maintained at about 0° C. The reaction completion is monitored by HPLC. The product is slowly poured into a 10% KHSO$_4$ solution. The solid is filtered, washed with a 10% KHSO$_4$ solution and water. The solid is dried in vacuo. To generate the deprotected peptide (SF1257-07; TFA.(D)Arg-(D)nL-(D)nL-(D)nL-OH) (SEQ ID NO:29), methanolic 1N LiOH (1 eq) is slowly added to a suspension of Boc-(D)Arg-(D)Nle-(D)Nle-(D)Nle-OMe.HCl (1 eq) (SEQ ID NO:29) in a mixture of water and methanol below 15° C. After about 30 min, the reaction mixture is allowed to warm up to room temperature. The completion of the hydrolysis is monitored by HPLC. The reaction mixture is acidified to pH 3 with 1N HCl at 15±2° C. Methanol is evaporated in vacuo and processed water is added to the mixture. The solid is filtered, washed with processed water, and dried in vacuo.

Synthesis of SF1257-08 (Boc-Gly-(D)Tyr-NH$_2$): HOBt (1 eq) is added to a solution of HCl.(D)Tyr-NH$_2$ (1.02 eq) in DMF. After complete dissolution TEA (~1.02 eq) is added at −7±2° C. without exceeding a pH value of 7. Boc-Gly-OH (1 eq) is slowly added to the mixture at −7±2° C. After complete dissolution, DCC (1.05 eq) in DMF is added by small portions at −7±2° C. The reaction mixture is stirred for about 60 min at −7±2° C. and then allowed to warm up to reach room temperature. The reaction completion is monitored by TLC. The DCU salt is removed by filtration and the filtrate is evaporated in vacuo. The oily residue is dissolved in butanol saturated in water, and washed with brine. Following extraction of the aqueous phase with butanol saturated in water, the combined organic phases are evaporated in vacuo. The oily residue is dried by azeotropic distillations with butanol. The product is precipitated with diisopropylether, filtered, and washed with diisopropylether. The solid is suspended in a mixture of butanol and diisopropyl ether (1/3, V/V), washed with diisopropyl ether and dried in vacuo. Deprotected peptide SF1257-09 (TFA.Gly-(D)Tyr-NH$_2$) is formed by slowly adding TFA (A×3 l) to a mixture of Boc-Gly-(D)Tyr-NH$_2$ (1 eq, A kg) and phenol (A×0.1 kg) in a mixture of toluene and THF, while maintaining the temperature at ≦18° C. After about 1 hr, the reaction mixture is allowed to warm up to room temperature. Following completion of cleavage, the reaction mixture is diluted with THF and then evaporated in vacuo. Residual TFA is removed by azeotropic distillation with toluene. The product is precipitated with diisopropylether, filtered, washed with diisopropylether, and dried in vacuo.

Synthesis of SF1257-10 (Boc-(D)Arg-(D)Nle-(D)Nle-(D)Nle-Gly-(D)Tyr-NH$_2$) (SEQ ID NO:30): DIPEA is slowly added at −5±2° C. to a solution of TFA.Gly-(D)Tyr-NH$_2$ (1 eq) in DMF until pH 8. Protected peptide Boc-(D)Arg-(D)Nle-(D)Nle-(D)Nle-OH (1 eq) (SEQ ID NO:29) and HOBt (0.88 eq) are added at −5±2° C. and the mixture is neutralized with DIPEA. PyBop (1.1 eq) is slowly added at −5±2° C. and the pH is adjusted to 7.5 with DIPEA at the same temperature. The coupling completion is monitored by HPLC. The reaction mixture is partially evaporated in vacuo, and the product precipitated in ethyl acetate. The precipitate is filtered and washed with ethyl acetate, a mixture of ethyl acetate and diisopropyl ether, and then diisopropyl ether. The solid is dried in vacuo. Removal of the protecting group is done by adding TFA (A×3 l) slowly to a mixture of peptide SF1257-10 (A kg), phenol (A×0.1 kg), toluene and THF while maintaining the temperature at ≦18° C. After about 30 min, the reaction mixture is allowed to warm up to room temperature. Following completion of cleavage, the reaction mixture is diluted with THF and then concentrated in vacuo. Residual TFA is removed by azeotropic distillation with toluene, and the deprotected peptide (SF1257-11) is precipitated with a mixture of petroleum ether and diisopropyl ether. The solid is filtered, washed with diisopropyl ether and dried in vacuo.

Synthesis of SF1257-12 (Boc-(D)Arg-(D)Nle-(D)Nle-(D)Nle-(D)Arg-(D)Nle-(D)Nle-(D)Nle-Gly-(D)Tyr-NH$_2$) (SEQ ID NO:1): A solution of SF1257-10 (1 eq) in DMF is adjusted to pH 7.5 with DIPEA at −5±2° C. Protected peptide Boc-(D)

Arg-(D)Nle-(D)Nle-(D)Nle-OH (SEQ ID NO:29) (1 eq) and HOBt (0.88 eq) are added at −5±2° C. The pH is adjusted to 7 with DIPEA, and PyBop (1.1 eq) is slowly added at −5±2° C. The pH is kept at 7.5 with DIPEA, and the reaction mixture is allowed to reach completion at −5±2° C. The reaction completion is monitored by HPLC. DMF is concentrated in vacuo and poured into a mixture of ethyl acetate and diisopropyl ether. The solid is filtered and washed with a mixture of ethyl acetate and petroleum ether and diisopropyl ether. The solid is dried in vacuo.

The deprotected peptide SF1257-13 (TFA-(D)Arg-(D)Nle-(D)Nle-(D)Nle-(D)Arg-(D)Nle-(D)Nle-(D)Nle-Gly-(D)Tyr-NH$_2$ (SEQ ID NO:1) is made by slowly adding TFA (A×3 l) to a mixture of SF1257-12 (A kg) and phenol (A×0.1 kg) in toluene and THF while maintaining the temperature at ≦18° C. The reaction mixture is allowed to warm up to room temperature. Following completion of cleavage, the solvent is diluted with THF and then concentrated in vacuo. Residual TFA is removed by azeotropic distillation with toluene. The residue is poured into a mixture of petroleum ether and diisopropyl ether. The solid is filtered, washed with diisopropyl ether and dried in vacuo.

Purification and isolation. The peptide is initially purified by reverse phase HPLC. The crude peptide (A=quantity expressed in grams) is dissolved in an 80% acetic acid solution (A×0.2 L). This solution is diluted with A×0.135 L of a mixture of acetonitrile and processed water (50/50, V/V) and successively filtered on a 10 μm and 0.6 μm filter. A new dilution is performed with processed water (2 volumes) and acetonitrile (150 mL/g) before loading onto the HPLC column.

For the HPLC purification, the stationary phase is C-8 Silica (Kromasil or equivalent) in a 450-600 mm diameter column. The gradient is an acetonitirile gradient of 50% solution B to 100% solution B over 55 min and 100% solution B for 20 min (Solution A: TFA/CH$_3$CN/H$_2$O: 0.1/5.0/94.9 (v/v/v); Solution B: TFA/CH$_3$CN/H$_2$O: 0.1/50.0/49.9 (v/v/v))

The primary purification step, which results in a peptide preparation of about 97% purity, is followed by a second purification by reverse phase HPLC using a similar type of stationary phase and column as used in the primary purification step. The peptide is purified using a gradient of 30% solution B to 70% solution B over 40 min and 70% B for 15 min. (Solution A: HOAc/CH$_3$CN/H$_2$O: 0.5/5/94.5 (v/v/v); Solution B: HOAc/CH$_3$CN/H$_2$O: 0.5/50/44.5 (v/v/v)). The secondary purification results in a peptide preparation of about 98%.

Concentration and desalting is done by preparative reverse phase HPLC on a 450-600 mm diameter column with a stationary phase of C-8 Silica (Kromasil or equivalent). The solvents were solution A—HOAc/CH$_3$CN/H$_2$O: 1/5/94 (v/v/v); solution B—HOAc/CH$_3$CN: 1/99 (v/v); and solution C—0.1M NH$_4$OAc pH 6.8 in CH$_3$CN/H$_2$O: 5/95 (v/v). The column washed successively with 100% A for 15 min, 100% C for 15 min., 100% A for 15 min., 100% C for 15 min, and 100% A for 15 min. The peptide was eluted with a solution of 60% A/40% B until complete elution was achieved.

Lyophilization and packaging. The purified RDP58 peptide is first concentrated on a thin-film evaporator in order to reduce the residual acetonitrile content before lyophilization.

The thin-film evaporator apparatus operates under reduced pressure. The device is composed of an evaporation column equipped with a heating jacket. Rotor agitation induces a fine liquid film in contact with the jacket. The contact time is very short. The vapor generated is distilled on a condenser with glycol refrigeration.

The technical parameters defined for this operation are:

|  | SMALL THIN-FILM |
| --- | --- |
| Jacket temperature: | 50 ± 3° C. |
| Rotor speed: | 550 ± 5 rpm |
| Vacuum: | ≦100 mbar |
| Glycol temperature: | ≦−16° C. |
| Flow rate: | 20 ± 1 L/h |

After evaporation of about 30%, the solution is filtered through a 0.2 μm fluorodyne cartridge (or equivalent). The filtered peptide solution is divided into lyophilization trays (maximum 1.67 l/tray), placed in the chamber of the freeze-dryer (2 trays per shelf), and lyophilised as follows: Lyophilization Cycle GT20 (a) freezing is done for 3 hrs at −40° C., (b) primary drying is for 7 hrs 20 min with a temperature gradient from −40° C. to +10° C. at a chamber pressure of 0.7 mbar and an additional 21 hrs at +10° C. at a chamber pressure: 0.7 mbar, and (c) secondary drying for 8 hrs with a temperature gradient from +10° C. to +20° C. at a chamber pressure of 0.7 mbar, followed by 14 hrs at a temperature of +20° C. and a pressure of 0.7 mbar, and finally 10 hrs at a temperature of +35° C. and a pressure of 0.1 mbar.

For Lyophilization Cycle GT200, the same lyophilization cycle as for the GT20 device is applied, the pressure being defined in percents in the GT200 device program: the 0.7 mbar pressure corresponds to a 52% programming and the 0.1 mbar pressure to a 33% programming.

When the cycle is completed, the chamber is vented with nitrogen. The powder is recovered in the isolator and directly transferred into the delumper. The delumping is performed in a conical stainless steel blender fitted with a mixing screw and a lump breaker and takes place in a controlled environment. A gentle rotation of the screw (80±5 rpm for GT20 and 100±5 rpm for GT200) is maintained for 30±5 min.

The powder is then recovered into the multilayer polyethylene bag. The bag is closed (double seal) with a heat sealer.

6.2 Example 2

Fill Formulations

Densification of the peptide. The peptide of the amino acid sequence

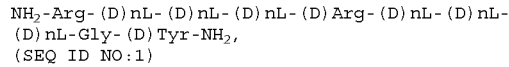

in the form of an acetate salt, is charged into a mortar and mixed using a pestle until the particles of peptide are broken down. Alternatively, the peptide in the form of an acetate salt, may be charged into a low shear mixer. Ethanol is added while mixing until a dense, but not too wet dough of peptide forms. The wet granulation is placed into a stainless steel tray, the wet lumps broken up manually, and the granules dried at room temperature. The dried granules are passed through a 100 or 40 mesh, preferably a 100 mesh, stainless steel screen to generate uniform granules for make the suspensions.

Fill Formulation. Labrafil M 1944 CS was demonstrated to provide enhanced dispersion of an RDP peptide (i.e., RDP58) having the sequence shown above. The RDP58 peptide was not soluble in Labrafil M 1944 CS, thus a stable suspension of the peptide was made using Colloidal Silicon Dioxide, USP (Aerosil 300) as a suitable dispersing agent. Bench trials were performed to determine the needed quantity of Aerosil 300, which would provide a sufficient viscosity increase to maintain the peptide uniformly suspended for a minimum of 24 hours while allowing the fill formulation to remain flowable or pumpable. The fill formulation for the a 100 mg RDP58 softgel capsule is the following:

| Ingredient | % w/w | mg/capsule |
| --- | --- | --- |
| RDP58 (granulated) | 17.54 | 100.00 |
| Labrafil M 1944 CS | 80.96 | 461.45 |
| Colloidal Silicon Dioxide, USP | 1.50 | 8.55 |
| Total | 100.00 | 570.00 |

A target capsule fill weight of 570 mg/capsule was selected, which has a fill volume of 9.7-10.0 minims. Therefore, a capsule size of 10 oval was selected to provide sufficient die cavity volume to contain the anticipated formulation fill volume. The fill formulation was compounded using standard pharmaceutical mixing techniques. The suspension was deaggregated using a colloid mill to assure all aggregates were below 180 mm and to improve the homogeneity of the suspension. This deaggregating step is optional for preparing the formulations.

6.3 Example 3

Gel Formulations

Gel Formulation. Burgundy (PMS 209C) was selected as the finished product color. A gel mass formulation was developed based on the target color and the finished product performance and is the following:

| Ingredient | Amount/100 kg gel mass |
| --- | --- |
| Gelatin, NF (150 Bloom Type B, Limed Bone) | 41.0 kg |
| Glycerin, 99.7% USP | 14.0 kg |
| Sorbitol Special, 76% | 9.0 kg |
| Purified Water, USP | 34.69 kg |
| White Opatint G-18000[1] | 982 kg |
| FD&C Red No. 40 | 0.318 kg |
| FD&C Blue No. 1 | 0.010 kg |

[1]White Opatint G-18000 is received as a 33.4% dispersion of Titanium Dioxide, USP in Glycerin, 99.7% USP.

The limed bone gelatin is domestically sourced and complies with both U.S. and EU regulations for TSE. The gel mass is produced using a hot melt process, which involves heating the glycerin and water portions to an appropriate temperature, then adding the powdered gelatin. The gelatin rapidly hydrates and dissolves forming a high-solids solution. Upon completion of dissolution, a vacuum is applied and entrained air is removed resulting in a clear, amber colored homogeneous solution with no evidence of air and/or particles. The colorants are then mixed into the gel solution, and a second deaeration is performed. Measuring the gel mass water content and viscosity determines the suitability of the gel mass for use in the encapsulation process. The gel mass is then discharged into heated holding tanks, where it is stored appropriately for further use in the softgel encapsulation process.

6.4 Example 4

Other Excipients

Pump and gel ribbon lubricant. Miglyol 812, food-grade lubrication oil, is used in the encapsulation process, which functions as a release agent for the positive displacement pump and the wet gel ribbon as it move over the metal contact surfaces as well as providing a wet seal at the encapsulation die/injection wedge interface, which assures no air is incorporated into the forming softgel capsule. Miglyol 812 (21 CFR 172.860) is classified as GRAS and is complies with the mid-chain triglyceride monograph in the European Pharmacopoeia (1997, 3$^{rd}$ edition). The Miglyol 812 is mechanically removed from the surface of the formed capsules using absorbent towels to promote the drying of the gel shell.

Capsule Release Agent. Newly formed softgel capsules are pliant and sticky after the surface lubricant oil is removed. A release agent, composed of Special Soybean Lecithin, NF (Centrocap® 162-US) in Miglyol 812 at a 1% w/w concentration is introduced during the tumble-drying of the capsules. The thin layer of deposited lecithin on the capsules surface prevents the capsules from sticking to each other during the tunnel drying process, where the capsules are place on drying trays in close proximity to each other. The 1% Lecithin/Miglyol mixture is compounded at the start of the encapsulation process and the solution is disposed after the encapsulation is completed. Special Soybean Lecithin, NF (Centrocap® 162-US) is released tested per the USP monograph.

Marking Ink. The finished product softgel capsules may be marked with pharmaceutical grade with a suitable ink, such as white ink (e.g., Opacode White S-1-7085). The individual ingredients composing the ink formulation are tested and released by the vendor, Colorcon, Inc. and comply with current USP and 21 CFR standards for excipients and marking inks.

6.5 Example 5

Formulations in Capsules

Composition of a single soft gel capsule containing 100 mg of the peptide is as follows:

| Ingredient Description | Compendial | Amt/Cap. | Function |
| --- | --- | --- | --- |
| Fill Composition | | | |
| RDP58 | N/A | 100.00 mg | Active |
| Oleoyl Macrogol-6 | EP, 3 ed. | 461.45 mg | Carrier/Surfactant/ |

-continued

| Ingredient Description | Compendial | Amt/Cap. | Function |
|---|---|---|---|
| Glycerides (Labrafil M 1944 CS) | DMF No. 4464 | | Bioenhancer |
| Colloidal Silicon Dioxide, USP (Aerosil 300) | USP | 8.55 mg | Dispersing agent |
| Fill Material Total | | 570.00 mg | |
| Gel Shell Ingredients | | | |
| Gelatin, NF 150 Bloom Limed Bone | NF 20 | 123.43 mg | Shell |
| Glycerin, 99.7%, USP[1] | USP | 44.11 mg | Plasticizer |
| Anhydrized Liquid Sorbitol (Sorbitol Special, 76%)[2] | NF (Vol. 29) DMF No. 11651 | 27.09 mg | Humectant |
| Purified Water, USP[3] | USP | 17.12 mg | Plasticizer |
| Titanium dioxide, USP | USP | 0.99 mg | Opacifier |
| FD&C Red No. 40 | Permitted | 0.96 mg | Colorant |
| FD&C Blue No. 1 | Permitted | 0.30 mg | Colorant |
| Gel Shell Total | | 214 mg | |

[1]Glycerin amount is adjusted to include the quantity carried into the formulation by the use of White Opatint G-18000.
[2]Prior to NF (Vol. 29, Sorbitol Special was non-compendial and tested was per an internal PII raw material specification. Notice of change occurred Apr. 23, 2003.
[3]In finished product capsules; the water content of the gel shell is estimated to be 8%, the water equilibrium content of gelatin.

6.6 Example 6

Effect of RDP58 Capsule Therapy in Primates Suffering From Colitis

RDP58 oral therapy is believed to have a beneficial effect on resolution of clinical signs of chronic colitis in primates suffering from a naturally occurring colitis like condition. In these studies, RDP58 was administered in aqueous form (i.e., powder dissolved in water) by oral gavage. The objective of the pilot study described in this example was to analyze the effect of administering RDP58 in capsule form to primates suffering from a chronic, naturally occurring, colitis-like condition. Data generated from this study was compared to data obtained from previous studies where RDP58 peptide was administered in aqueous form.

Methods. Four cynomolgus monkeys, with documented clinical histories of chronic and naturally occurring colitis, were selected for the study. All animals were monitored for 7 days before initiating therapy. Animals were dosed with one capsule (approximately 13 mg per capsule) every day, starting on Day 0, for 14 days. A commercially available cat pilling gun was used. Disease activity was monitored using stool quality scores. The scoring system used was the following: 1=Normal; 2=Loose stool; 3=Watery diarrhea; and 4=Bloody diarrhea. Response is defined as an improvement in stool quality score by at least 1 point.

Animals were physically examined twice per day. After 14 days, RDP58 therapy was stopped and animals were monitored for 7 additional days. Stool quality was documented through this period.

Results. RDP58 capsule therapy had positive effects on disease activity in all animals. Animal MCY33560 showed an immediate response to peptide treatment. Normal stool quality scores were present after end of therapy. With sporadic variation in scores after day 20, stool scores returned to normal on day 25 and remained normal until day 37 (end of study). This animal was not re-treated with RDP58 peptide.

Animal 33558 was dosed starting on day 0 and an immediate response to therapy was observed. Although variable, the animal remained relatively free of diarrhea. RDP58 therapy was stopped on day 14 after which the animal remained normal for 4-5 days. There was a gradual relapse of diarrhea and the animal was re-treated with RDP58 starting on day 23. Response to therapy was immediate and the animal had normal stool scores up to day 28. On day 31, the animal was diagnosed with Giardia infection and was withdrawn from the study.

Animal MCY33639 similarly had an immediate positive response to RDP58 therapy. After stopping therapy, however, there was a gradual return of diarrhea. On day 23, the animal was re-treated with RDP58 and once again, an immediate positive response was noted and the animal remained free of diarrhea until day 37, when the study ended.

Animal MCY33636 was initiated on RDP58 therapy on day 0. Although response was immediate, there was a relatively longer duration before which the animal showed normal stool quality scores. Therefore, treatment period for this animal was extended to day 21, instead of the 14 day regimen used for other animals. This animal did show normal stool quality for 8 days but after the end of therapy (day 21), during the observation period, there was relapse of diarrhea leading to severe dehydration. This animal could not be re-treated and was subsequently euthanized.

Conclusions. Oral RDP58 peptide therapy, in a capsule composition comprising an RDP58 peptide, a suspending agent, and a dispersing agent, in primates suffering from a naturally occurring colitis-like condition resulted in a positive therapeutic response that was similar to previously reported observations of RDP58 therapy in an aqueous composition. None of the animals studied showed negative side effects, and dosing was well tolerated.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to explain the principles of the invention and its practical application, to thereby enable others skilled in the art to utilize the invention and various embodiments with various modifications as are suited to the particular use contemplated.

All patents, patent applications, publications, and references cited herein are expressly incorporated by reference to the same extent as if each individual publication or patent application was specifically and individually indicated to be incorporated by reference.

What is claimed is:

1. A pharmaceutical composition, comprising: a RDP peptide, a suspending agent, and a dispersing agent, which form a liquid suspension of said bioactive peptide compound, wherein said RDP peptide has the amino acid sequence Arg-nL-nL-nL-Arg-nL-nL-nL-Gly-Tyr    (SEQ ID NO:1)

and wherein said dispersing agent is colloidal silicon dioxide.

2. The composition according to claim 1, wherein said suspending agent is selected from the group consisting of sorbitan oleate, monolein/propylene glycol, polyglycolized glycerides, polyethoxylated castor oil, polyethoxylated hydrogenated caster oil, polyoxyethylene stearic acid and esters thereof, polyoxyethylene-polyoxypropylene co-polymers, propylene glycol caprylic-capric acid diesters, carprylic/capric acid mono and diglycerides, sorbitan fatty acid esters, stigmasterol, polyethylene glycols, and compatible mixtures thereof.

3. The composition according to claim 2, wherein said polyglycolized glyceride is an oleoyl macrogol glyceride.

4. A composition comprising the acetate salt of the RDP peptide NH$_2$-Arg-nL-nL-nL-Arg-nL-nL-nL-Gly-Tyr-NH$_2$, a suspending agent, and a dispersing agent, which forms a liquid suspension of said RDP peptide, wherein said dispersing agent is colloidal silicon dioxide and wherein at least one amino acid of said peptide, other than glycine, is a D-isomer.

5. The composition according to claim 4, further comprising a capsule which encapsulates said suspension.

6. The composition according to claim 5, wherein said capsule is selected from the group consisting of a hard capsule, a soft capsule, a starch capsule, and a hydroxypropyl methycellulose (HPMC) gelatin capsule.

7. The composition according to claim 5, wherein said capsule is coated with an enteric coating.

8. A pharmaceutical composition comprising:
   (a) a bioactive peptide or salt thereof, wherein said bioactive peptide has the structure NH$_2$-(D)Arg-(D)nL-(D)nL-(D)nL-(D)Arg-(D)nL-(D)nL-(D)nL-Gly-(D)Tyr-NH$_2$;
   (b) a suspending agent, and
   (c) a dispersing agent, wherein said dispersing agent is colloidal silicon dioxide; and wherein said peptide, said suspending agent, and said dispersing agent form a liquid suspension.

9. The pharmaceutical composition according to claim 8, further comprising a soft gelatin capsule that encapsulates said suspension.

10. The pharmaceutical composition according to claim 8, wherein said suspending agent is selected from the group consisting of sorbitan oleate, monolein/propylene glycol, polyglycolized glycerides, polyethoxylated castor oil, polyethoxylated hydrogenated caster oil, polyoxyethylene stearic acid and esters thereof, polyoxyethylene-polyoxypropylene co-polymers, propylene glycol caprylic-capric acid diesters, carprylic/capric acid mono and diglycerides, sorbitan fatty acid esters, stigmasterol, polyethylene glycols, and compatible mixtures thereof.

11. The pharmaceutical composition according to claim 10, wherein said polyglycolized glyceride is an oleoyl macrogol glyceride.

12. The pharmaceutical composition according to claim 11, wherein said oleoyl macroglyceride is selected from the group consisting of Labrafil 1944CS™; Labrafil 1966CS™; and Labrafil 1969CS™.

13. The pharmaceutical composition according to claim 8, wherein said bioactive peptide is in the form of an acetate salt.

14. The pharmaceutical composition according to claim 8, further comprising a capsule that encapsulates said suspension, wherein said capsule is selected from the group consisting of a hard capsule and a starch capsule.

15. The pharmaceutical composition according to claim 9, wherein said soft gelatin capsule is a hydroxypropyl methylcellulose (HPMC) gelatin capsule.

16. A method of treating inflammatory bowel disease comprising administering to a subject in need thereof an effective amount of the composition of claim 1, 4 or 8.

* * * * *

```
                        SEQUENCE LISTING

<160> NUMBER OF SEQ ID NOS: 31

<210> SEQ ID NO 1
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Xaa at positions 2 to 4 are norleucine
<220> FEATURE:
<221> NAME/KEY: MISC_FEATURE
<222> LOCATION: (6)..(8)
<223> OTHER INFORMATION: The Xaa at positions 6 to 8 are norleucine

<400> SEQUENCE: 1

Arg Xaa Xaa Xaa Arg Xaa Xaa Xaa Gly Tyr
1               5                   10

<210> SEQ ID NO 2
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Xaa at position 1 can be any basic amino
      acid, preferably lysine or arginine
<220> FEATURE:
<221> NAME/KEY: MISC_FEATURE
<222> LOCATION: (2)..(4)
<223> OTHER INFORMATION: The Xaa at positions 2 to 4 can be any
      non-polar aliphatic or aromatic amino acid of from 5 to 6 carbon
      atoms, preferably any amino acid other than a polar aliphatic
      amino acid
<220> FEATURE:
<221> NAME/KEY: MISC_FEATURE
<222> LOCATION: (5)..(5)
<223> OTHER INFORMATION: The Xaa at position 5 can be any basic amino
      acid, preferably lysine or arginine
<220> FEATURE:
<221> NAME/KEY: MISC_FEATURE
<222> LOCATION: (6)..(8)
<223> OTHER INFORMATION: The Xaa at positions 6 to 8 can be any
      non-polar aliphatic or aromatic amino acid of from 5 to 6 carbon
      atoms, preferably any amino acid other than a polar aliphatic
      amino acid
<220> FEATURE:
<221> NAME/KEY: MISC_FEATURE
<222> LOCATION: (9)..(9)
<223> OTHER INFORMATION: The Xaa at position 9 can be glycine, or any
      basic amino acid, or an aliphatic hydrophobic amino acid of from 5
      to 6 carbon atoms

<400> SEQUENCE: 2

Xaa Xaa Xaa Xaa Xaa Xaa Xaa Xaa Xaa Tyr
1               5                   10

<210> SEQ ID NO 3
```

```
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Xaa at position 2 can be an uncharged
      aliphatic or aromatic amino acid, preferably a non-polar aliphatic
      or aromatic amino acid
<220> FEATURE:
<221> NAME/KEY: MISC_FEATURE
<222> LOCATION: (3)..(4)
<223> OTHER INFORMATION: The Xaa at positions 3 to 4 can be any
      non-polar aliphatic or aromatic amino acid of from 5 to 6 carbon
      atoms, preferably any amino acid other than a polar aliphatic
      amino acid
<220> FEATURE:
<221> NAME/KEY: MISC_FEATURE
<222> LOCATION: (6)..(8)
<223> OTHER INFORMATION: The Xaa at positions 6 to 8 can be any
      non-polar aliphatic or aromatic amino acid of from 5 to 6 carbon
      atoms, preferably any amino acid other than a polar aliphatic
      amino acid
<220> FEATURE:
<221> NAME/KEY: MISC_FEATURE
<222> LOCATION: (9)..(9)
<223> OTHER INFORMATION: The Xaa at position 9 can be glycine, or any
      basic amino acid, or an aliphatic hydrophobic amino acid of from 5
      to 6 carbon atoms

<400> SEQUENCE: 3

Arg Xaa Xaa Xaa Arg Xaa Xaa Xaa Xaa Tyr
1               5                   10

<210> SEQ ID NO 4
<211> LENGTH: 10
<212> TYPE: PRT
<213> ORGANISM: Artificial
<220> FEATURE:
<223> OTHER INFORMATION: Synthetic

<400> SEQUENCE: 4

Arg Leu Leu Leu Arg Leu Leu Leu Gly Tyr
1               5                   10

<210> SEQ ID NO 5
<211> LENGTH: 10
<212> TYPE: PRT
<213> ORGANISM: Artificial
<220> FEATURE:
<223> OTHER INFORMATION: Synthetic

<400> SEQUENCE: 5

Arg Val Leu Leu Arg Leu Leu Leu Gly Tyr
1               5                   10

<210> SEQ ID NO 6
<211> LENGTH: 10
<212> TYPE: PRT
<213> ORGANISM: Artificial
<220> FEATURE:
<223> OTHER INFORMATION: Synthetic

<400> SEQUENCE: 6

Arg Ile Leu Leu Arg Leu Leu Leu Gly Tyr
1               5                   10

<210> SEQ ID NO 7
<211> LENGTH: 10
```

```
<212> TYPE: PRT
<213> ORGANISM: Artificial
<220> FEATURE:
<223> OTHER INFORMATION: Synthetic

<400> SEQUENCE: 7

Arg Leu Val Leu Arg Leu Leu Leu Gly Tyr
1               5                   10

<210> SEQ ID NO 8
<211> LENGTH: 10
<212> TYPE: PRT
<213> ORGANISM: Artificial
<220> FEATURE:
<223> OTHER INFORMATION: Synthetic

<400> SEQUENCE: 8

Arg Leu Ile Leu Arg Leu Leu Leu Gly Tyr
1               5                   10

<210> SEQ ID NO 9
<211> LENGTH: 10
<212> TYPE: PRT
<213> ORGANISM: Artificial
<220> FEATURE:
<223> OTHER INFORMATION: Synthetic

<400> SEQUENCE: 9

Arg Leu Leu Val Arg Leu Leu Leu Gly Tyr
1               5                   10

<210> SEQ ID NO 10
<211> LENGTH: 10
<212> TYPE: PRT
<213> ORGANISM: Artificial
<220> FEATURE:
<223> OTHER INFORMATION: Synthetic

<400> SEQUENCE: 10

Arg Leu Leu Ile Arg Leu Leu Leu Gly Tyr
1               5                   10

<210> SEQ ID NO 11
<211> LENGTH: 10
<212> TYPE: PRT
<213> ORGANISM: Artificial
<220> FEATURE:
<223> OTHER INFORMATION: Synthetic

<400> SEQUENCE: 11

Arg Leu Leu Leu Arg Val Leu Leu Gly Tyr
1               5                   10

<210> SEQ ID NO 12
<211> LENGTH: 10
<212> TYPE: PRT
<213> ORGANISM: Artificial
<220> FEATURE:
<223> OTHER INFORMATION: Synthetic

<400> SEQUENCE: 12

Arg Leu Leu Leu Arg Ile Leu Leu Gly Tyr
1               5                   10

<210> SEQ ID NO 13
<211> LENGTH: 10
<212> TYPE: PRT
```

```
<213> ORGANISM: Artificial
<220> FEATURE:
<223> OTHER INFORMATION: Synthetic

<400> SEQUENCE: 13

Arg Leu Leu Leu Arg Leu Val Leu Gly Tyr
 1               5                  10

<210> SEQ ID NO 14
<211> LENGTH: 10
<212> TYPE: PRT
<213> ORGANISM: Artificial
<220> FEATURE:
<223> OTHER INFORMATION: Synthetic

<400> SEQUENCE: 14

Arg Leu Leu Leu Arg Leu Ile Leu Gly Tyr
 1               5                  10

<210> SEQ ID NO 15
<211> LENGTH: 10
<212> TYPE: PRT
<213> ORGANISM: Artificial
<220> FEATURE:
<223> OTHER INFORMATION: Synthetic

<400> SEQUENCE: 15

Arg Leu Leu Leu Arg Leu Leu Val Gly Tyr
 1               5                  10

<210> SEQ ID NO 16
<211> LENGTH: 10
<212> TYPE: PRT
<213> ORGANISM: Artificial
<220> FEATURE:
<223> OTHER INFORMATION: Synthetic

<400> SEQUENCE: 16

Arg Leu Leu Leu Arg Leu Leu Ile Gly Tyr
 1               5                  10

<210> SEQ ID NO 17
<211> LENGTH: 10
<212> TYPE: PRT
<213> ORGANISM: Artificial
<220> FEATURE:
<223> OTHER INFORMATION: Synthetic

<400> SEQUENCE: 17

Arg Trp Leu Leu Arg Leu Leu Leu Gly Tyr
 1               5                  10

<210> SEQ ID NO 18
<211> LENGTH: 10
<212> TYPE: PRT
<213> ORGANISM: Artificial
<220> FEATURE:
<223> OTHER INFORMATION: Synthetic

<400> SEQUENCE: 18

Arg Leu Trp Leu Arg Leu Leu Leu Gly Tyr
 1               5                  10

<210> SEQ ID NO 19
<211> LENGTH: 10
<212> TYPE: PRT
<213> ORGANISM: Artificial
```

<220> FEATURE:
<223> OTHER INFORMATION: Synthetic

<400> SEQUENCE: 19

Arg Leu Leu Trp Arg Leu Leu Leu Gly Tyr
1               5                   10

<210> SEQ ID NO 20
<211> LENGTH: 10
<212> TYPE: PRT
<213> ORGANISM: Artificial
<220> FEATURE:
<223> OTHER INFORMATION: Synthetic

<400> SEQUENCE: 20

Arg Leu Leu Leu Arg Trp Leu Leu Gly Tyr
1               5                   10

<210> SEQ ID NO 21
<211> LENGTH: 10
<212> TYPE: PRT
<213> ORGANISM: Artificial
<220> FEATURE:
<223> OTHER INFORMATION: Synthetic

<400> SEQUENCE: 21

Arg Leu Leu Leu Arg Leu Trp Leu Gly Tyr
1               5                   10

<210> SEQ ID NO 22
<211> LENGTH: 10
<212> TYPE: PRT
<213> ORGANISM: Artificial
<220> FEATURE:
<223> OTHER INFORMATION: Synthetic

<400> SEQUENCE: 22

Arg Leu Leu Leu Arg Leu Leu Trp Gly Tyr
1               5                   10

<210> SEQ ID NO 23
<211> LENGTH: 10
<212> TYPE: PRT
<213> ORGANISM: Artificial
<220> FEATURE:
<223> OTHER INFORMATION: Synthetic

<400> SEQUENCE: 23

Arg Tyr Leu Leu Arg Leu Leu Leu Gly Tyr
1               5                   10

<210> SEQ ID NO 24
<211> LENGTH: 10
<212> TYPE: PRT
<213> ORGANISM: Artificial
<220> FEATURE:
<223> OTHER INFORMATION: Synthetic

<400> SEQUENCE: 24

Arg Leu Tyr Leu Arg Leu Leu Leu Gly Tyr
1               5                   10

<210> SEQ ID NO 25
<211> LENGTH: 10
<212> TYPE: PRT
<213> ORGANISM: Artificial
<220> FEATURE:

```
<223> OTHER INFORMATION: Synthetic

<400> SEQUENCE: 25

Arg Leu Leu Tyr Arg Leu Leu Leu Gly Tyr
1               5                   10

<210> SEQ ID NO 26
<211> LENGTH: 10
<212> TYPE: PRT
<213> ORGANISM: Artificial
<220> FEATURE:
<223> OTHER INFORMATION: Synthetic

<400> SEQUENCE: 26

Arg Leu Leu Leu Arg Tyr Leu Leu Gly Tyr
1               5                   10

<210> SEQ ID NO 27
<211> LENGTH: 10
<212> TYPE: PRT
<213> ORGANISM: Artificial
<220> FEATURE:
<223> OTHER INFORMATION: Synthetic

<400> SEQUENCE: 27

Arg Leu Leu Leu Arg Leu Tyr Leu Gly Tyr
1               5                   10

<210> SEQ ID NO 28
<211> LENGTH: 10
<212> TYPE: PRT
<213> ORGANISM: Artificial
<220> FEATURE:
<223> OTHER INFORMATION: Synthetic

<400> SEQUENCE: 28

Arg Leu Leu Leu Arg Leu Leu Tyr Gly Tyr
1               5                   10

<210> SEQ ID NO 29
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Xaa at positions 2 to 4 are norleucine

<400> SEQUENCE: 29

Arg Xaa Xaa Xaa
1

<210> SEQ ID NO 30
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Xaa at positions 2 to 4 are norleucine

<400> SEQUENCE: 30

Arg Xaa Xaa Xaa Gly Tyr
1               5
```

```
<210> SEQ ID NO 31
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Xaa at position 1 is a basic amino acid,
      preferably arginine or lysine
<220> FEATURE:
<221> NAME/KEY: MISC_FEATURE
<222> LOCATION: (2)..(4)
<223> OTHER INFORMATION: The Xaa at positions 2 to 4 are norleucine
<220> FEATURE:
<221> NAME/KEY: MISC_FEATURE
<222> LOCATION: (5)..(5)
<223> OTHER INFORMATION: The Xaa at position 5 is a basic amino acid,
      preferably arginine or lysine
<220> FEATURE:
<221> NAME/KEY: MISC_FEATURE
<222> LOCATION: (6)..(8)
<223> OTHER INFORMATION: The Xaa at positions 6 to 8 are norleucine
<220> FEATURE:
<221> NAME/KEY: MISC_FEATURE
<222> LOCATION: (9)..(9)
<223> OTHER INFORMATION: The Xaa at position 9 is arginine, lysine,
      or glycine, preferably glycine

<400> SEQUENCE: 31

Xaa Xaa Xaa Xaa Xaa Xaa Xaa Xaa Xaa Tyr
1               5                   10
```